(12) United States Patent  
Rinner

(10) Patent No.: US 11,471,205 B2  
(45) Date of Patent: *Oct. 18, 2022

(54) MULTIPLE FULCRUM CUTTER

(71) Applicant: Pacific Instruments, Inc., Honolulu, HI (US)

(72) Inventor: James A. Rinner, Franksville, WI (US)

(73) Assignee: Pacific Instruments, Inc., Honolulu, HI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/159,112

(22) Filed: Jan. 26, 2021

(65) Prior Publication Data

US 2021/0145496 A1 May 20, 2021

Related U.S. Application Data

(63) Continuation of application No. 15/417,647, filed on Jan. 27, 2017, now Pat. No. 10,905,488.

(60) Provisional application No. 62/287,562, filed on Jan. 27, 2016.

(51) Int. Cl.  
*A61B 17/88* (2006.01)  
*B26B 13/26* (2006.01)  
*B23D 29/02* (2006.01)  
*B26B 13/00* (2006.01)

(52) U.S. Cl.  
CPC .......... *A61B 17/8863* (2013.01); *B23D 29/02* (2013.01); *B26B 13/26* (2013.01); *B26B 13/00* (2013.01)

(58) Field of Classification Search  
CPC ............................ B26B 29/02; A61B 17/8863  
See application file for complete search history.

(56) References Cited

U.S. PATENT DOCUMENTS

| D226,548 S | * | 3/1973 | Burgeson | D8/58 |
| 5,404,616 A | * | 4/1995 | Carmien | B25G 1/04 |
| | | | | 16/422 |
| 8,613,145 B2 | * | 12/2013 | Poole | B26B 17/02 |
| | | | | 30/191 |
| 10,905,488 B2 | * | 2/2021 | Rinner | B26B 13/26 |
| 2014/0090527 A1 | * | 4/2014 | Behlen | A61B 17/8863 |
| | | | | 83/13 |

* cited by examiner

*Primary Examiner* — Ghassem Alie  
*Assistant Examiner* — Samuel A Davies  
(74) *Attorney, Agent, or Firm* — Brainspark Associates, LLC

(57) ABSTRACT

Disclosed are devices, systems and methods for modifying, cutting and/or shaping surgical fixation components of various configurations, including spinal fixation rods and related components.

20 Claims, 19 Drawing Sheets

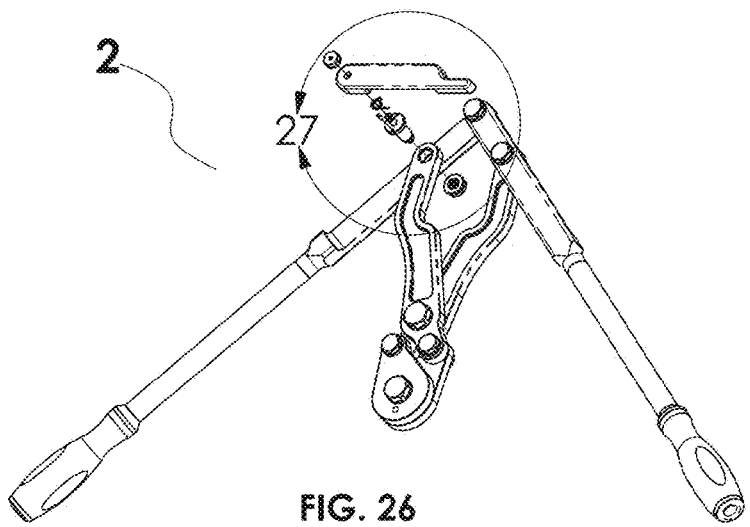
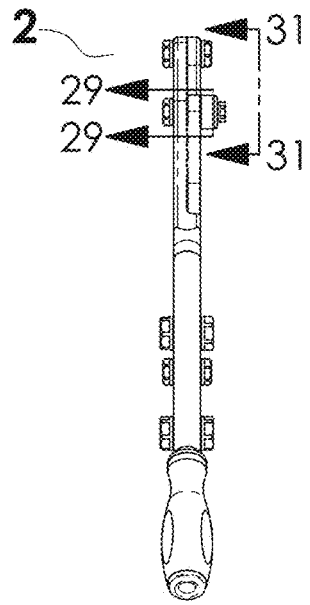
FIG. 26
FIG. 28
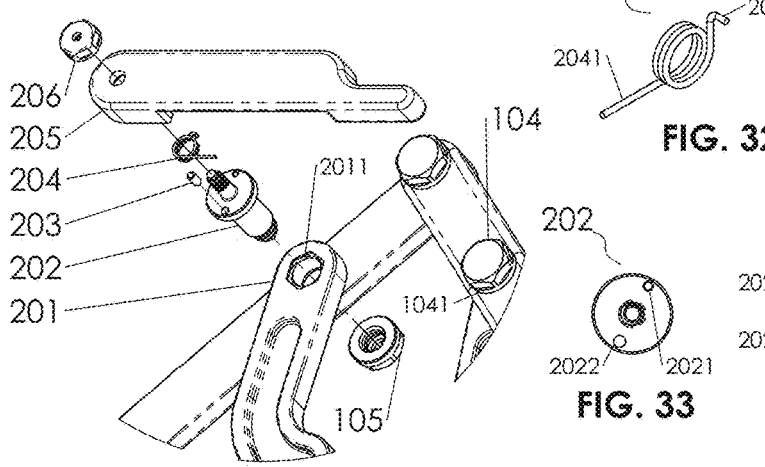
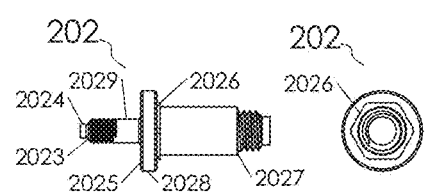
FIG. 27
FIG. 32
FIG. 33
FIG. 34
FIG. 35
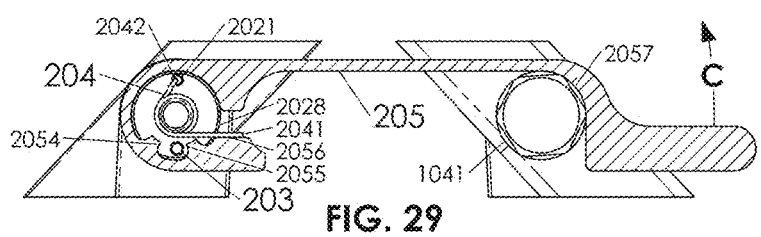
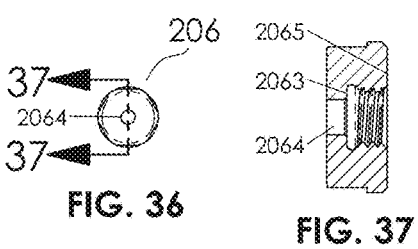
FIG. 29
FIG. 36
FIG. 37
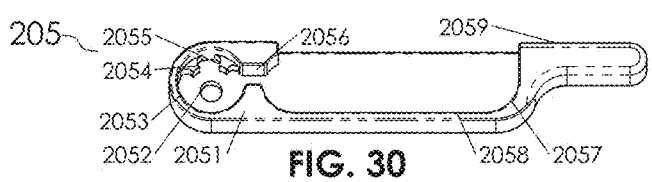
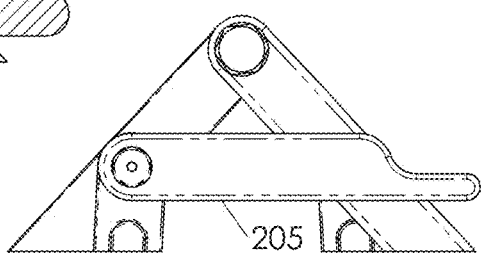
FIG. 30
FIG. 31

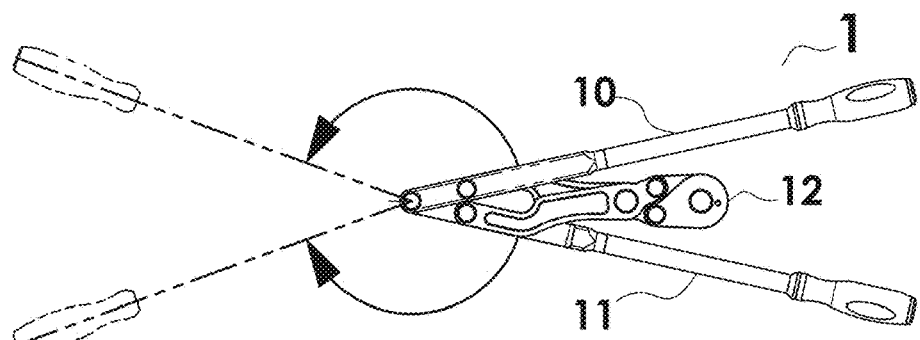
FIG. 38
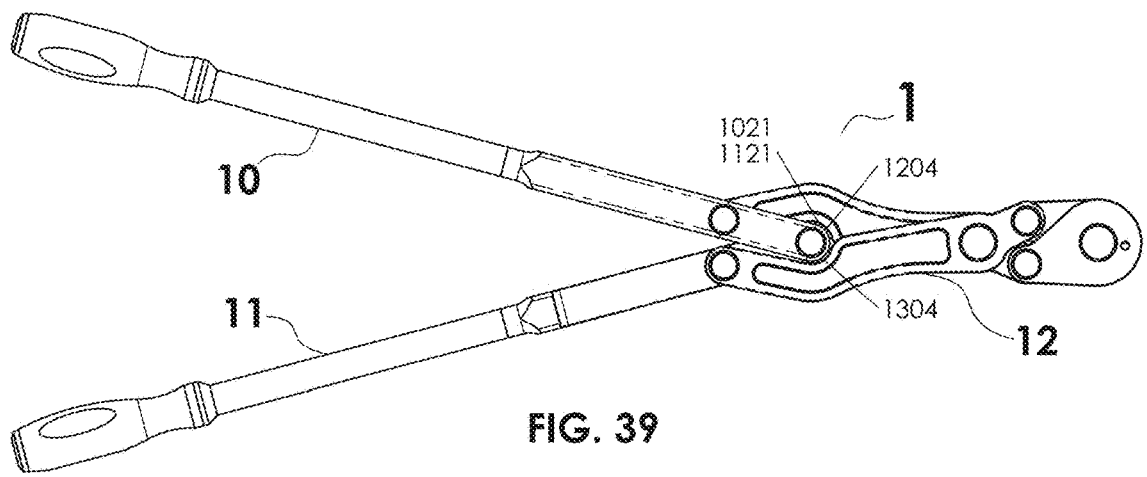
FIG. 39
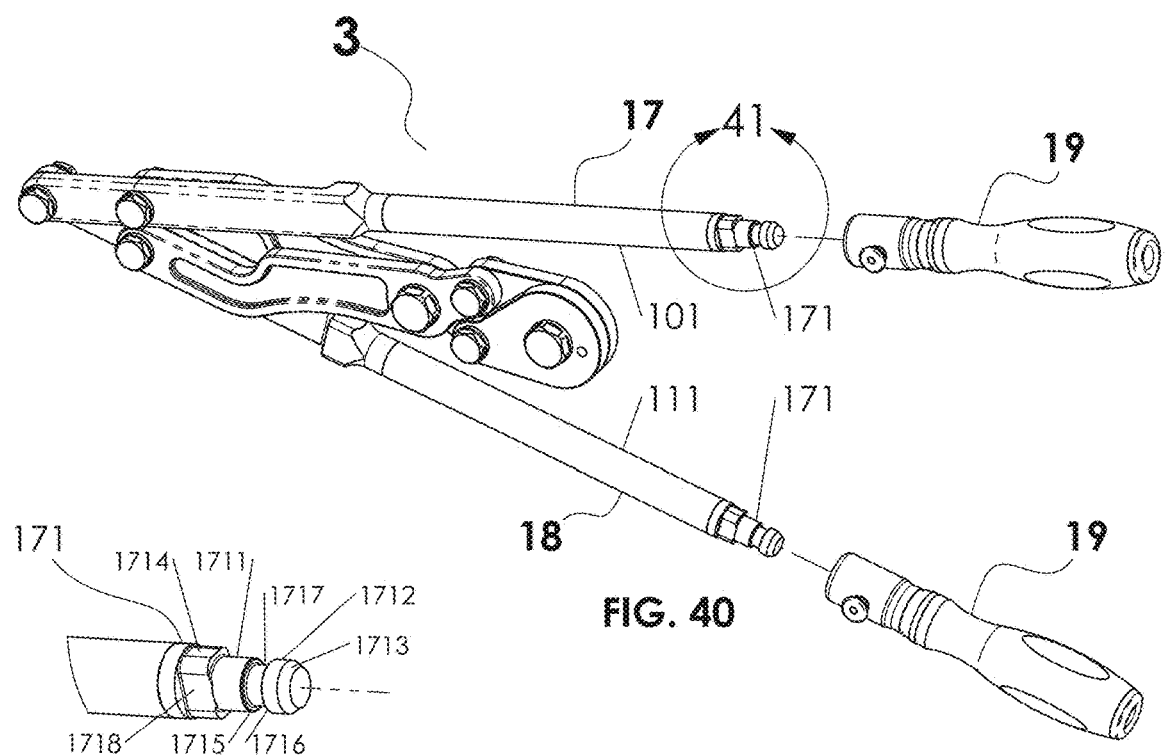
FIG. 40
FIG. 41

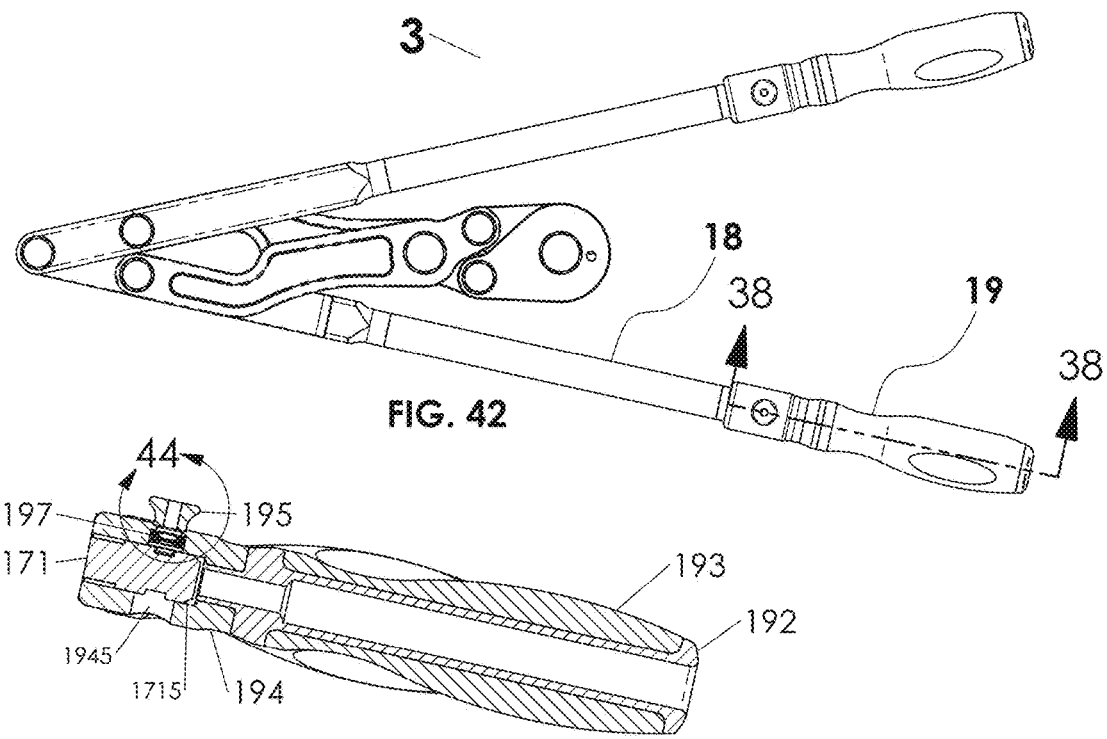
FIG. 42
FIG. 43
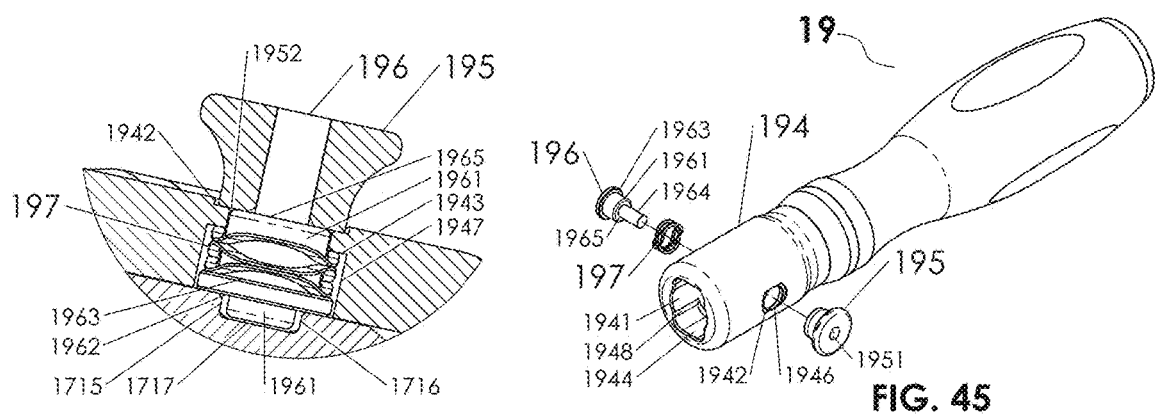
FIG. 44
FIG. 45
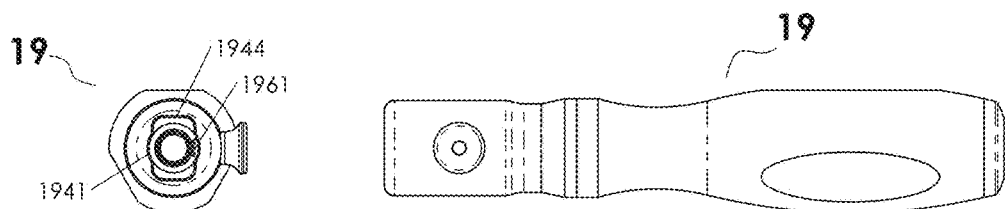
FIG. 46
FIG. 47

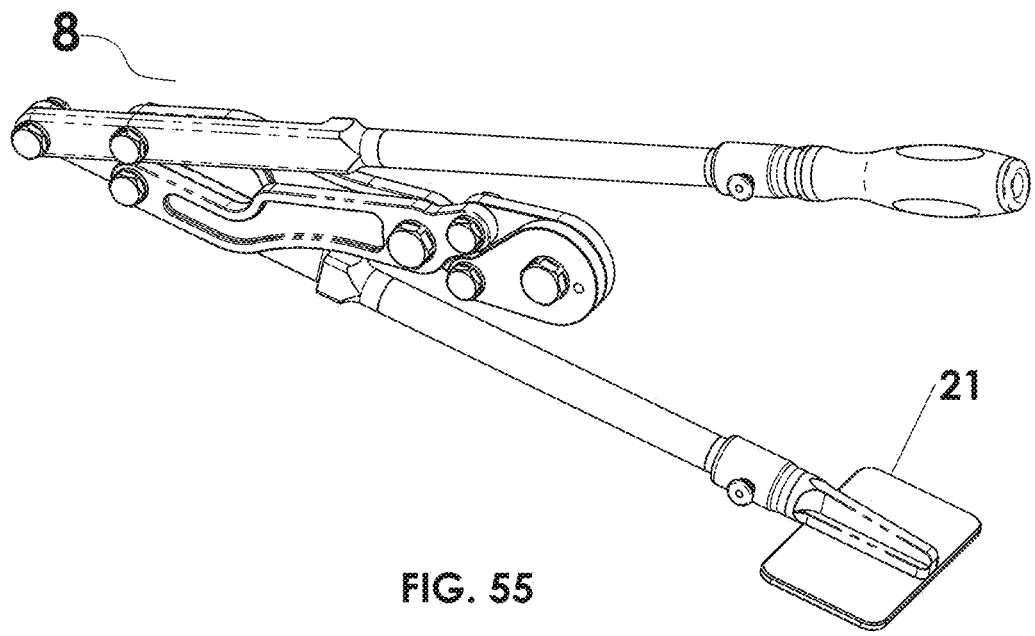
FIG. 55
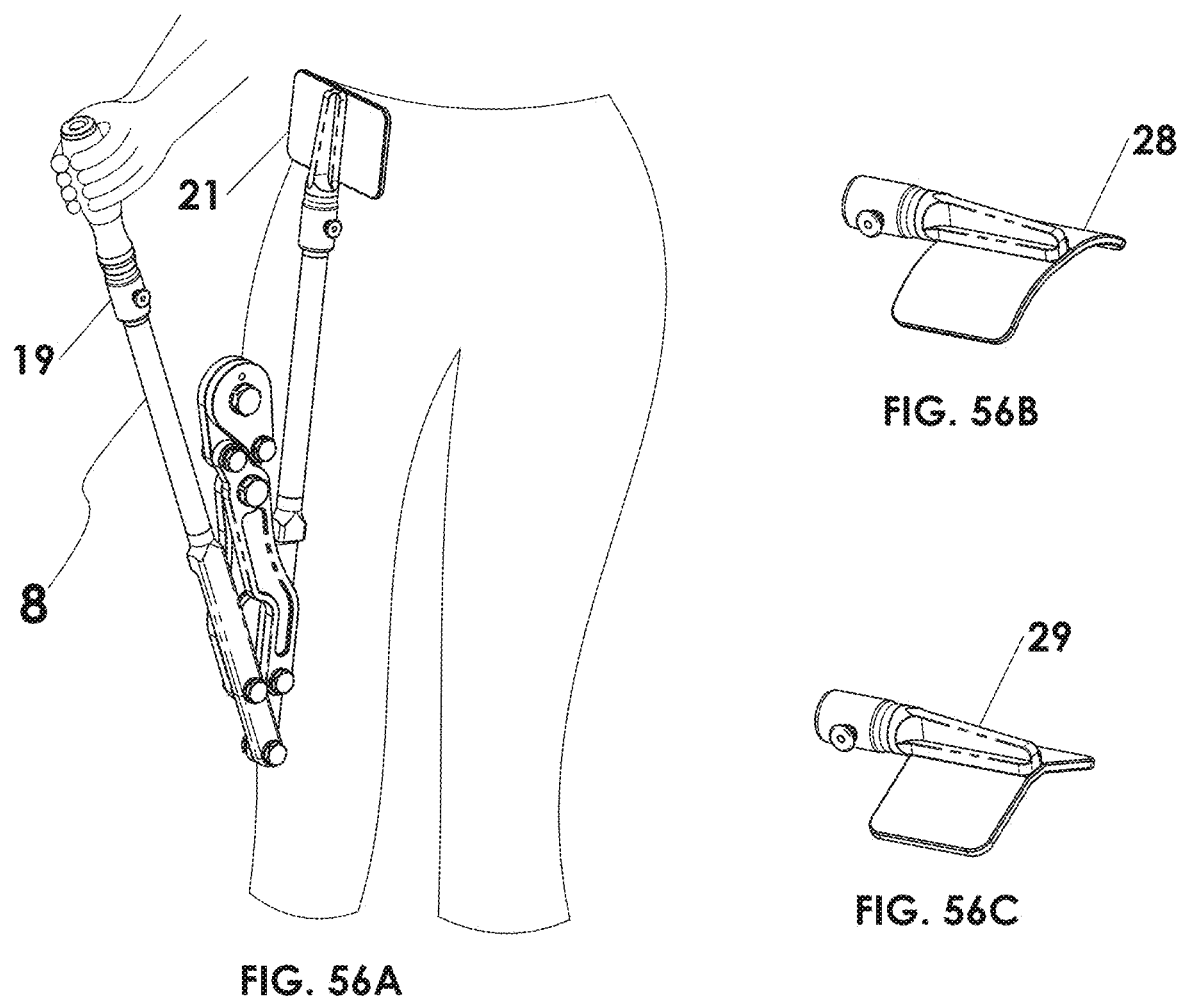
FIG. 56A
FIG. 56B
FIG. 56C

MULTIPLE FULCRUM CUTTER

CROSS-REFERENCE TO RELATED APPLICATIONS

This application is a continuation application of U.S. patent application Ser. No. 15/417,647 entitled "Multiple Fulcrum Cutter," filed Jan. 27, 2017, which in turn claims the benefit of U.S. Provisional Patent Application Ser. No. 62/287,562 entitled "Multiple Fulcrum Cutter," filed Jan. 27, 2016. The disclosures of each of these references are incorporated by reference herein in their entireties.

TECHNICAL FIELD

Disclosed are devices, systems and associated methods for cutting devices used for modifying, cutting and/or shaping surgical fixation components of various configurations, including spinal fixation rods and related components.

BACKGROUND OF THE INVENTION

Surgical cutters used for manually modifying various shaped objects and/or implant have been available in the art for many years. With the advent of new alloys of stronger and stiffer material, however, the leverage and/or mechanical advantages needed to cut and/or otherwise modify these new materials is often much higher. Users of such devices are having a difficult time cutting these materials with currently-available tools and methods.

SUMMARY OF THE INVENTION

The present invention includes devices, systems and cutting methods for use with devices having a cutting or other moveable mechanism at an end of the device that can be similar in some respects to existing devices in the prior art, but which also incorporates multiple sets of lever arms and/or other leverage arrangements to desirably increase the amount of force applied to the material being cut while reducing size, bulk, complexity and/or required force input for the device. In various embodiments, the addition of supplemental sets of lever arms can desirably increase the length of the cutter the invention's handles (desirably providing increased mechanical advantage) while concurrently allowing the cutting mechanism to assume a variety of configurations and/or positions relative to the tool, including placement of the cutting mechanism between the actuating handles (to desirably shorten the overall length of the instrument) or alternatively extending outward from the devices, without requiring any significant disassembly or reassembly of device components.

These and other objects, advantages, and features of the disclosure will be apparent from the following description, considered along with the accompanying drawings.

BRIEF DESCRIPTION OF THE DRAWINGS

The present invention will be more understood in the detailed description and the accompanying drawings.

FIG. 26 depicts a partially-exploded perspective view of another embodiment of a cutting tool constructed in accordance with various teachings of the present invention;

FIG. 27 depicts an enlarged exploded partial view of the embodiment from FIG. 26, taken along arc 27;

FIG. 28 depicts a right-side plan view of the embodiment of FIG. 26;

FIG. 29 depicts an enlarged cross-sectional view of the embodiment of FIG. 28, taken along plane 29-29;

FIG. 30 depicts an opposite perspective view of a lever 205 from the embodiment of FIG. 27;

FIG. 31 depicts a partial plan view of the embodiment of FIG. 28, taken along plane 31-31;

FIG. 32 depicts a perspective view of a spring from FIG. 27;

FIG. 33 depicts a left planar view of a shaft from FIG. 27;

FIG. 34 depicts a side planar view of a shaft from FIG. 27;

FIG. 35 depicts a right planar view of a shaft from FIG. 27;

FIG. 36 depicts a planar view of a nut from FIG. 27;

FIG. 37 depicts an enlarged cross-sectional view of the nut from FIG. 36, taken along plane 37-37;

FIG. 38 depicts a top planar view of FIG. 1, showing exemplary first and second alternative positions for operation of this embodiment of a cutting device via rotation of the handles;

FIG. 39 depicts a top planar view of the embodiment of FIG. 38, showing the completed rotation of the handles to the second alternative position;

FIG. 40 depicts a perspective view of another alternative embodiment of a cutting tool, with removable handle sections and/or handgrips;

FIG. 41 depicts an enlarged view of an engagement portion of the embodiment of FIG. 40, taken about arc 41;

FIG. 42 depicts a top planar view of the embodiment of FIG. 40;

FIG. 43 depicts an enlarged cross-sectional view of a handle of the embodiment of FIG. 42, taken along plane 38-38;

FIG. 44 depicts an enlarged partial cross-sectional view of an exemplary engagement mechanism from FIG. 43, taken about arc 44;

FIG. 45 depicts a partial exploded perspective view of an exemplary embodiment of a detachable handle section or handgrip, such as shown in FIG. 42;

FIG. 46 depicts a left plan view of the handgrip of FIG. 45;

FIG. 47 depicts a top plan view of the handgrip of FIG. 45;

FIG. 55 depicts a perspective view of another alternative embodiment of a cutting tool incorporating various features of the present invention, where the tool can be utilized in a horizontal orientation, such as on a table with a flat plate stabilizer;

FIG. 56A depicts a perspective view of another alternative embodiment of a cutting tool incorporating various features of the present invention, where the tool can be utilized in a vertical orientation, such as against a user's body part or other vertical surface with a flat plate stabilize;

FIG. 56B depicts a perspective view of another alternative embodiment of a stabilizer incorporating a curved plate;

FIG. 56C depicts a perspective view of another alternative embodiment of a stabilizer incorporating an angled plate;

DETAILED DESCRIPTION OF THE DRAWINGS

In the following detailed description, for purposes of explanation, numerous specific details are set forth to provide a thorough understanding of the various embodiments of the disclosure. Those of ordinary skill in the art will realize that these various embodiments are illustrative only and are not intended to be limiting in any way. In addition, for clarity purposes, not all of the routine features of the embodiments described herein may be shown or described for every alternative embodiment. One of ordinary skill in the art would readily appreciate that in the development of any such actual implementation, numerous implementation-specific decisions may be required to achieve specific design objectives. These design objectives may vary from one implementation to another and from one developer to another, and the variations thereof are contemplated and included in the present disclosure.

Function

The intended use of the various embodiments of the cutter is intended for handheld use but the mechanical functions can also be used in a device powered by electricity, gears, hydraulic, pneumatic and/or other sources of power, as well as various combinations thereof. In addition, while various of the embodiments disclosed herein may be shown as operated while "closing" the handles (i.e., bringing the handles closer together can initiate a cutting action in some embodiments), it should also be understood that other directions of handle travel and/or cutter motion (i.e., "opening," pulling apart and/or otherwise rotating the handles or cutting surfaces) could be utilized to initiate cutting actions with similar and/or different functions and/or magnitudes, if desired, as well as various combinations of opening and closing actions to accomplish various of the objectives disclosed herein.

Components

Those of ordinary skill in the art should realize that the various embodiments described herein are illustrative only, are not intended to be limiting in any way and the various components described herein in various embodiments can be combined and subtracted to fit the specific needs of various designs of cutters or other devices.

Desirably, the overall dimensions and/or thickness or width of the cutter (as well as the remaining components of the cutter) can be customized or particularized to an individual item that requires cutting or other modification.

Figure 1:
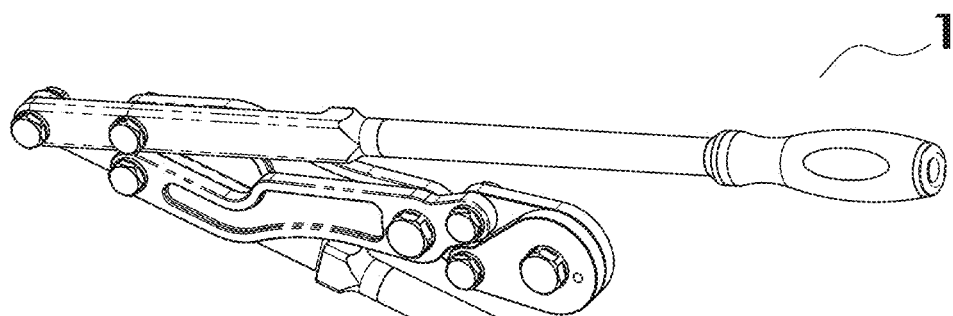
FIG. 1 depicts a perspective view of one embodiment of a cutting device in a collapsed or finished position.

FIG. 1 depicts a perspective view of one exemplary embodiment 1 of a cutting device or "cutter." The cutter 1 is shown in a "compacted" position, with the cutter head subassembly positioned between the two handles operated by the user (not shown). Because the arrangement and type of cutter jaw utilized in this embodiment (121 and 131—SEE FIG. 4), this embodiment allows a user to operate the handles while keeping the item within the cutting field at a very close proximity to the operator (i.e., the object to be cut can be positioned between the first fulcrum or lever and the operating ends of the first handle set). Another advantage for this compact position is a reduced overall dimension for the cutting tool, which lends to a compact storage envelope.

Figure 2:
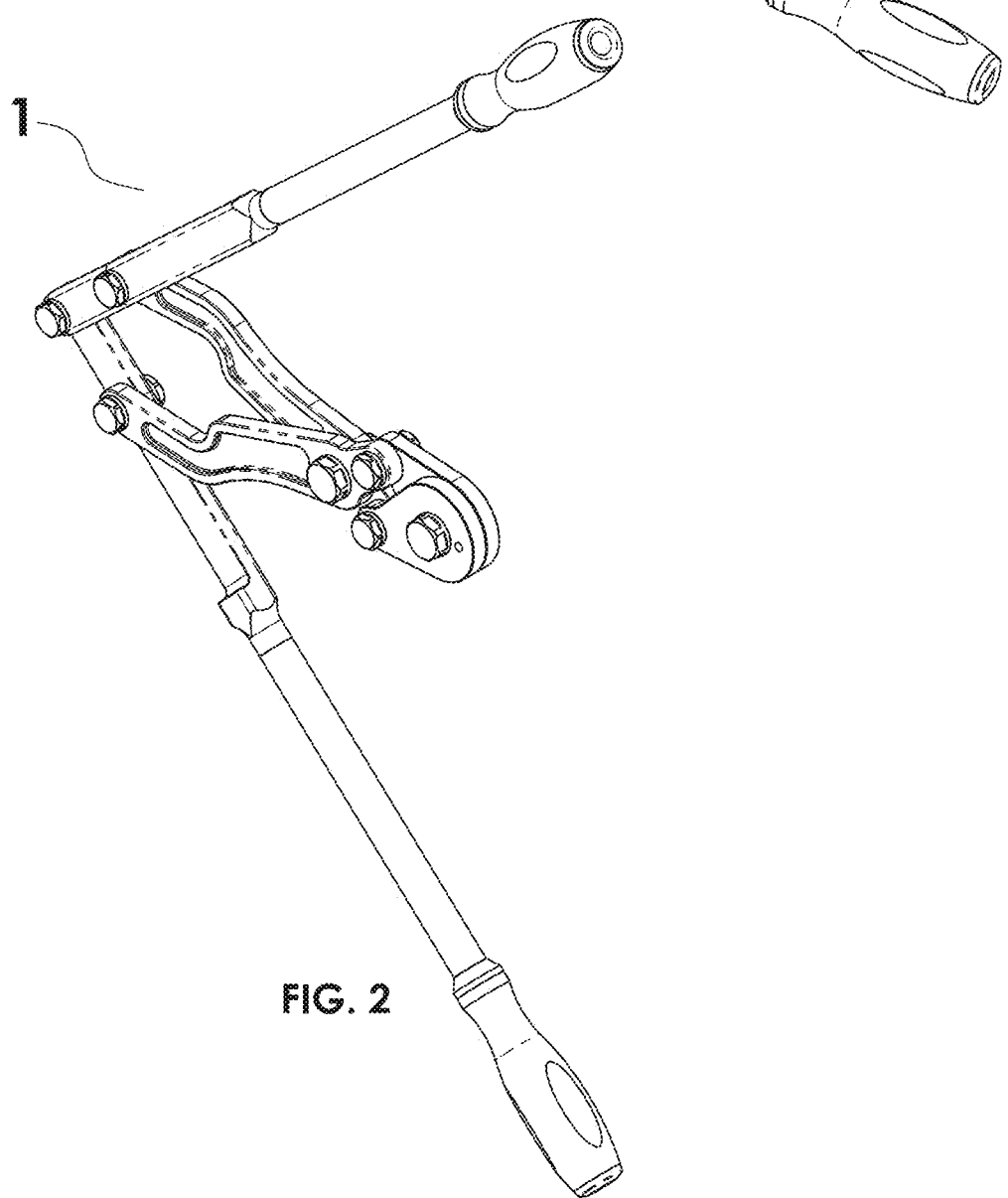
FIG. 2 depicts a perspective view of the embodiment of FIG. 1 in an open position.
Figure 3:
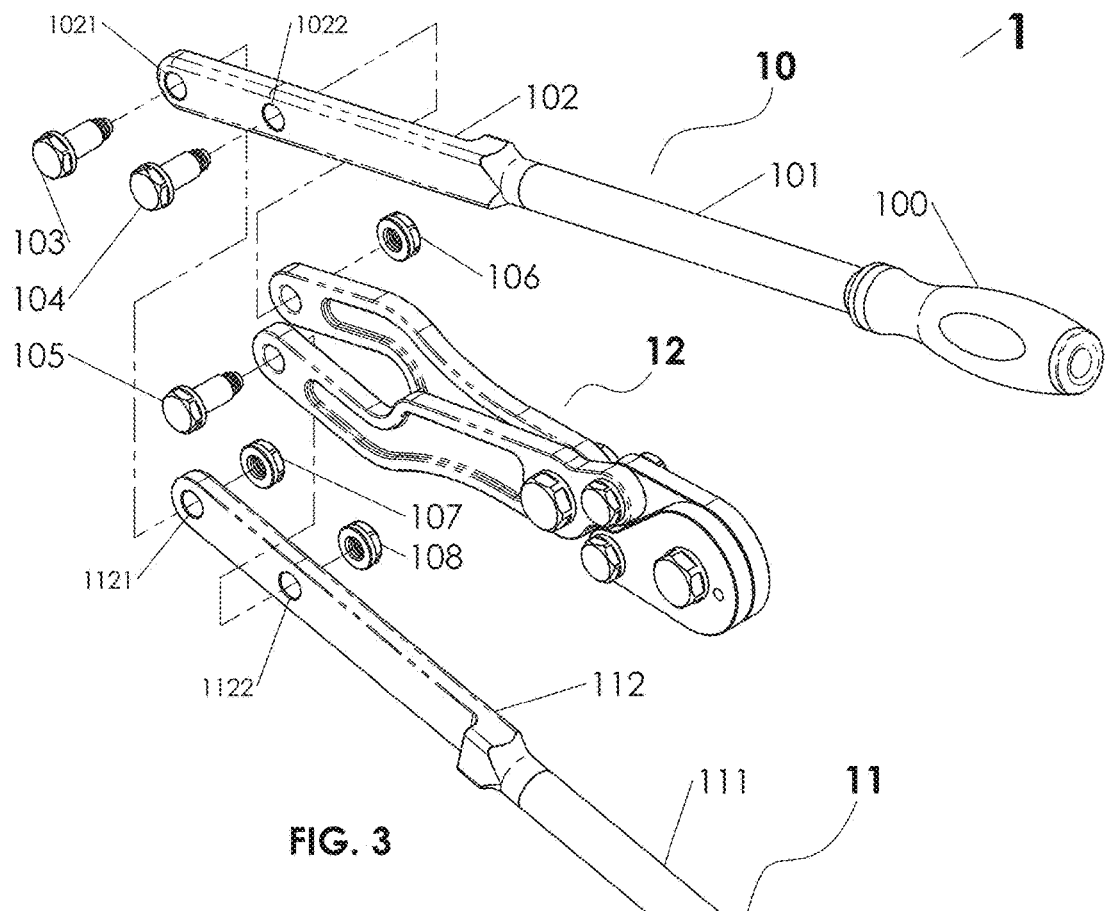
FIG. 3 depicts a semi-exploded perspective view of the embodiment of FIG. 1.
Figure 4:
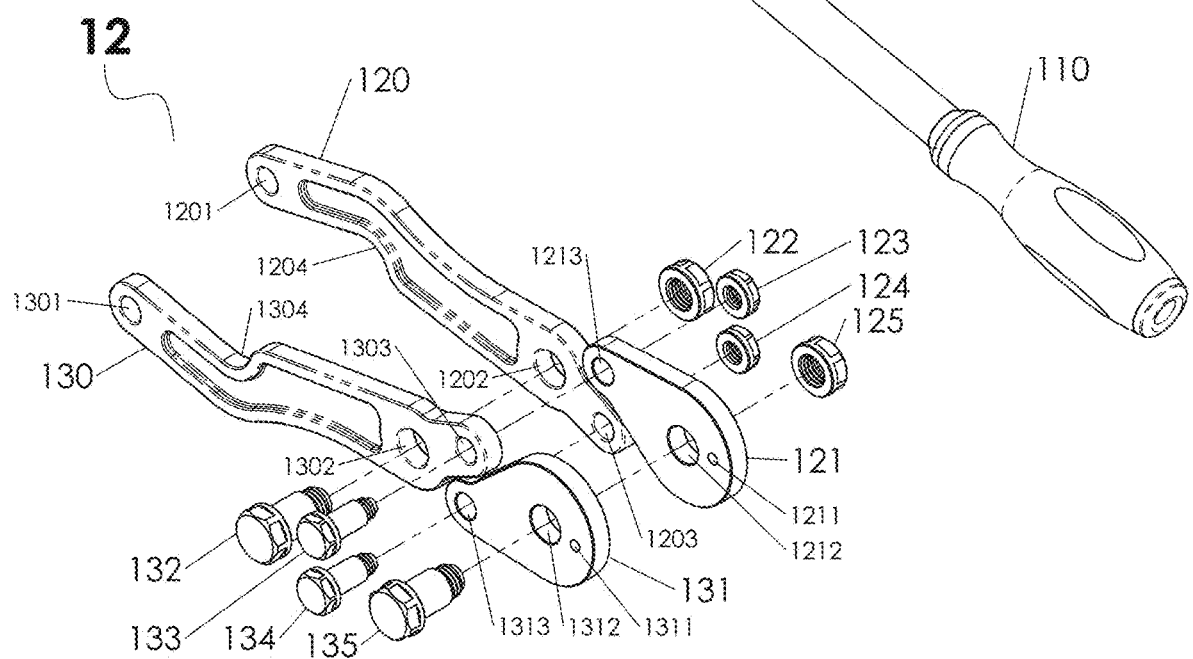
FIG. 4 depicts an exploded view of sub-assembly 12 of the embodiment of FIG. 1.

FIG. 2 depicts the cutter embodiment 1 in an open or starting position. To further explain this position, the various components shown in FIGS. 3 and 4 are arranged and positioned to form a chain or linkage of multiple lever arms that desirably move with respect to one another as the handgrips 100 and 110 are moved closer and/or further from each other in an arcuate manner. A series of individual linkages comprises the following connections, starting with the main arm assemblies 10 and 11 (comprising handgrips 100 and 110, handles 101 and 111 and arms 102 and 112, respectively). There are also various references to components being pivotally attached through various holes in the components. These pivoting features can be held together using various connections, including threaded screws or bolts 103, 104, 105, 132, 133, 134 and 135 and nuts 106, 107, 108, 122, 123, 124 and 125, respectively. The various connections are desirably designed in such a manner that the threaded bolts and screws do not "clamp" the components together in an inflexible arrangement, but rather to allow relatively free rotation of the bolts and screws in their respective mating holes. Those skilled in the art should understand that, even though threads are used to secure the rotating screws and nuts to each other, there are other mean, such as, but not limited to, press fits, welds or clevis pins, that can be used to connect various components in a desirable manner.

In the disclosed embodiment, the handgrips 100 and 110 are attached to handles 101 and 111, respectively, which are then attached to arms 102 and 112, respectively, while the arms are pivotally attached to each other through the holes 1021 and 1121. Next, the arms 102 and 112 are pivotally mounted through the holes 1022 and 1122 with holes 1201 and 1301 of levers 120 and 130, respectively. As best seen in FIG. 4, levers 120 and 121 form part of an lever and cutter sub-assembly 12. The levers 120 and 130, of sub-assembly 12, are pivotally mounted to each other through holes 1202 and 1302. The jaws 121 and 131 are pivotally mounted to the levers 120 and 130 through the lever holes 1203 and 1303 and the jaw holes 1213 and 1313, respectively. The jaws 121 and 131 are pivotally mounted to each other through the holes 1212 and 1312.

Various embodiments of the present invention employ multiple levers and/or fulcrums, linked to one another in specified manners, to create a significant mechanical advantage from a user input not found in other surgical cutting devices.

Figure 5:
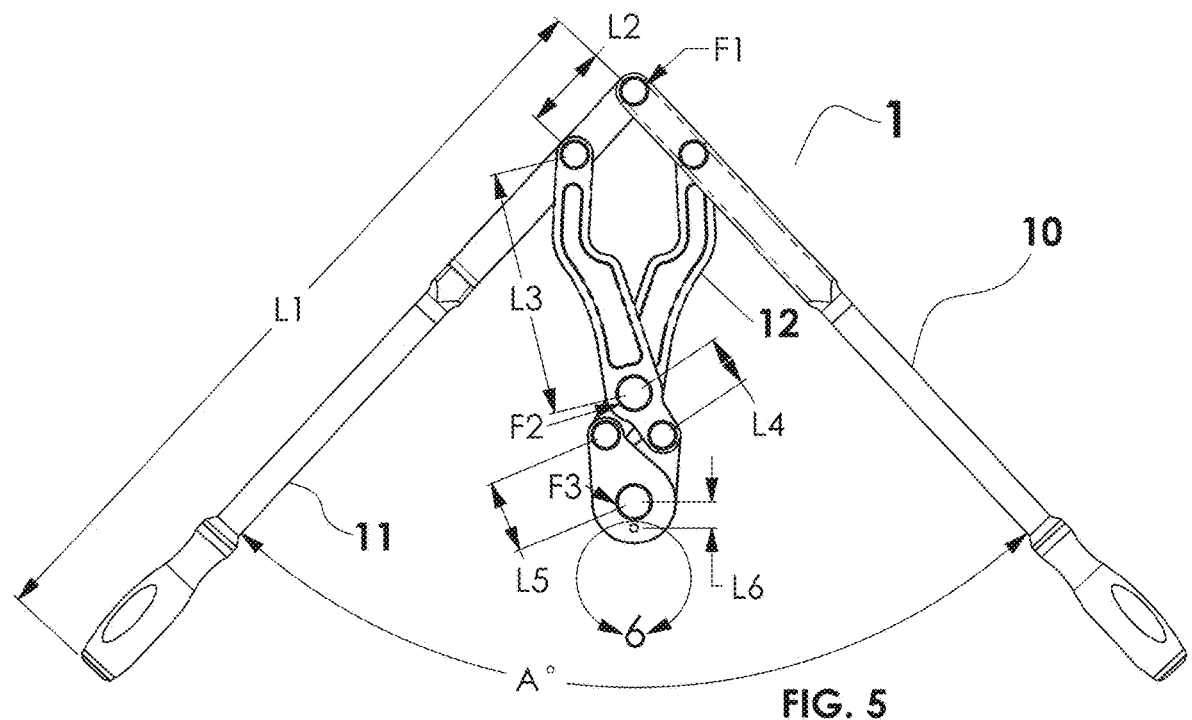
FIG. 5 depicts a top planar view of the embodiment of FIG. 2.

With primary reference to the embodiment of FIGS. 3 through 5, the following levers and fulcrums are disclosed and described, with each arrangement desirably providing a user input with a progressively increasing mechanical advantage: MA1, MA2 and MA3.

MA1=L1/L2 when the fulcrum is at F1. If we use the hypothetical lengths for the levers where L1=20 and L2=2, we can desirably have a resulting mechanical advantage of up to 10. In this example, both of the lever arms 10 and 11 can function as "Second-Order" levers, in that the "applied load" (from the user) and the "effort" (which is applied to the next lever set) is positioned on the same side of the fulcrum or pivot (F1), but applied in opposite directions.

MA2=L3/L4 when the fulcrum is at F2. If we use the hypothetical lengths for the levers where L3=5 and L4=1, we can desirably have a resulting mechanical advantage of up to 5. In this example, both of the lever arms 120 and 130 can function as "First-Order" levers, in that the fulcrum or pivot (F2) is positioned between the "applied load" (from levers 10 and 11) and the "effort" (which is applied to the next further lever set).

MA3=L5/L6 when the fulcrum is at F3. If we use the hypothetical lengths for the levers where L5=2.25 and L6=0.75, we can desirably have a resulting mechanical advantage of up to 3. In this example, both of the lever arms 121 and 131 can function as "First-Order" levers, in that the fulcrum or pivot (F3) is positioned between the "applied load" (from levers 120 and 130) and the "effort" (which is applied to cut or otherwise modify the workpiece). In at least one alternative embodiment, however, these lever arms could function as "Second-Order" levers, wherein the fulcrum or pivot (F3) could alternatively be positioned on one side of the "applied load" and the "effort", or multiple holes could be employed about the fulcrum such that the lever arms might function as First-Order and/or Second-Order levers, depending upon which hole set is selected for the cutting operation (see FIGS. 19 through 22, 60 and 61).

In the above described exemplary system, if a user applies 50 units of force on the end of L1 (by squeezing the levers 11 and 10 together) and using MA1=10, the user can apply a resulting 500 units of force (50×10) at the pivot where L3 connects. With 500 units of force applied at the end of L3, this is translated to a resulting 2500 units of force (500×5) at the end of L5, because MA2=5. Finally, 2500 units of force being applied to the end of L5 can result in 7500 units of force at the end of L6. Thus, the final mechanical advantage for the described device and system is 10×5×3 or 150. Previously, to accomplish this with a single set of lever arms and a single fulcrum, the length for L1 would have to be fifteen times longer than L2, or 300 (in this example).

Figure 6:
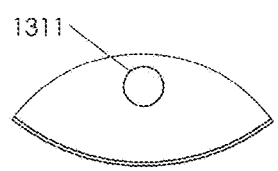
FIG. 6 depicts an enlarged partial view of a cutter head from FIG. 5 about arc 6.
Figure 67B:
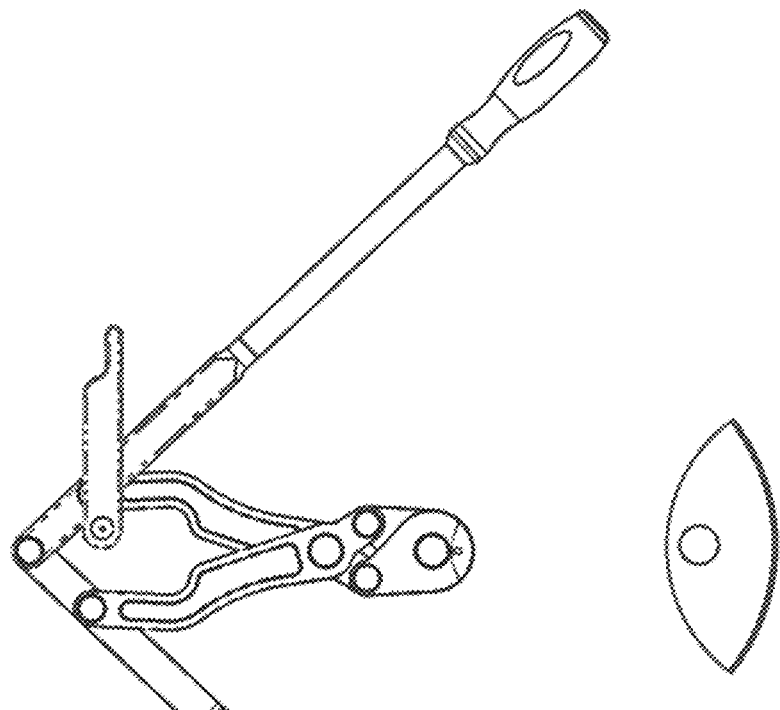
FIG. 67B depicts a side view of the cutting device of FIG. 67A in a second handle position.

FIG. 5 depicts one embodiment of a cutting device constructed in accordance with various teachings of the present invention, with the device in a starting or "open" position, as shown by Angle A. This position desirably aligns the hole 1211 of jaw 121 and hole 1311 of jaw 131 with each other, which allows a material and/or implant to be cut to pass through the holes 1211 and 1311, as shown on the enlarged partial view in FIG. 6. This may also be referred to as a "second position" for the cutting device (see FIG. 67B).

Figure 8:
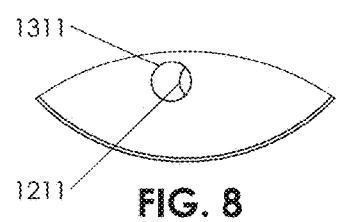
FIG. 8 depicts an enlarged partial view of the cutter head from FIG. 7 about arc 8.
Figure 7:
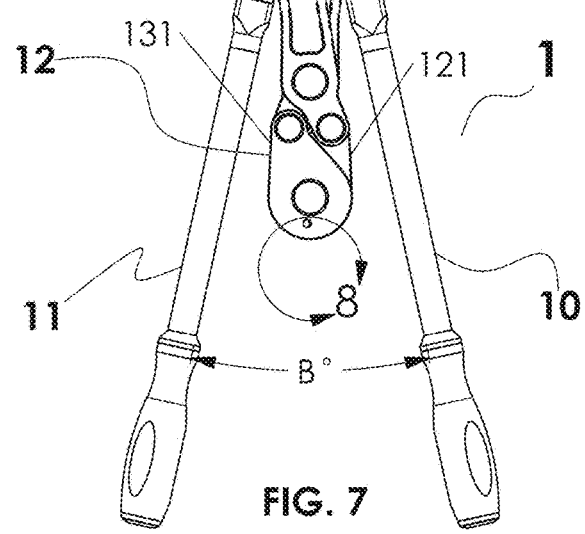
FIG. 7 depicts a top plane view of the embodiment of FIG. 1.
Figure 67A:
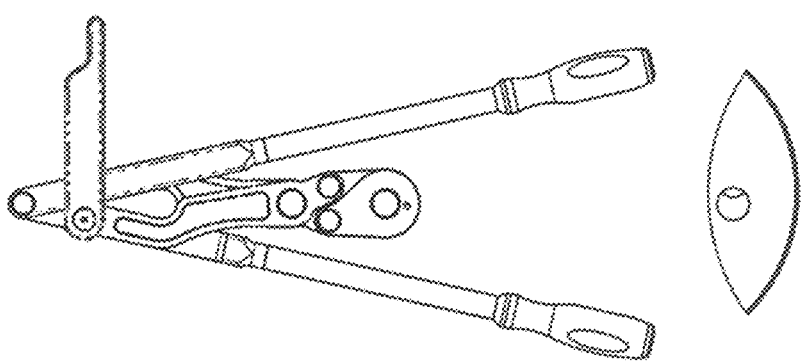
FIG. 67A depicts a side view of one embodiment of a cutting device in a first handle position.
Figure 67C:
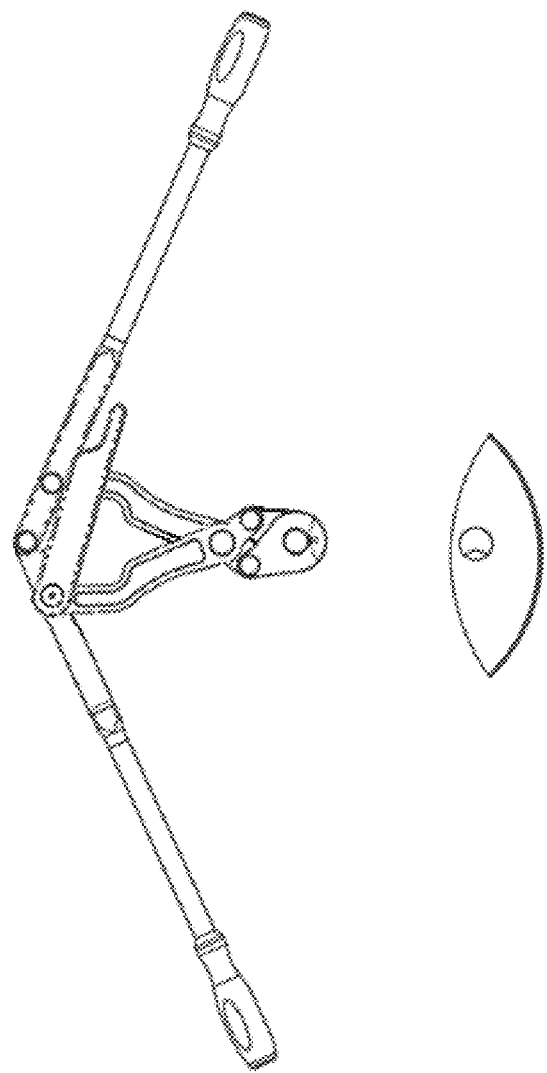
FIG. 67C depicts a side view of the cutting device of FIG. 67A in a third handle position.

FIG. 7 depicts the cutting device embodiment in the finished or "closed" position, such as shown by Angle B. In this embodiment, a cutting process occurs when a cutting force is applied to the material in the holes 1211 of jaw 121 and hole 1311 of jaw 131, with the holes rotating opposite to each other (in response to movement of the arms 10 and 11), which ultimately causes the material within the holes to fail (with material failure desirably occurring proximate to the junction of the two holes). The amount of force necessary to cause such material failure, and the exact location or locations of such failure is often determined by the properties of the material being cut. Where the cutting action is a shearing action, many material will completely shear before the cutters (i.e., the inner surfaces or "edges" of the aligned holes) pass half-way through the material. A material that is notch sensitive, like alloyed titanium, will often completely shear sooner than a more ductile material, like aluminum or stainless steel. The enlarged partial view of FIG. 8 shows an exemplary view of the holes having passed each other's center-axis (with some small portion of the openings of holes still aligned). This may also be referred to as a "first position" for the cutting device (see FIG. 67A) where arms 10 and 11 are being brought closer together, with movement of the arms 10 and 11 in an opposing direction away from each other leading to a "third position" for the cutting device (see FIG. 67C).

Figure 9:
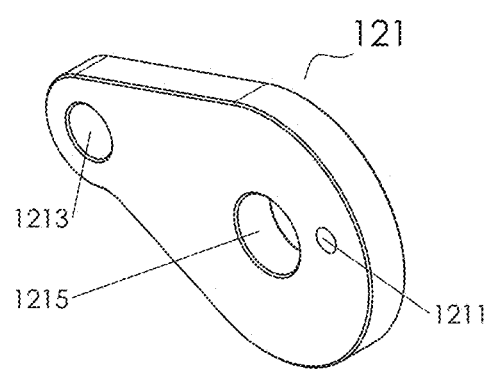
FIG. 9 depicts a perspective view of one embodiment of a cutter jaw, such as a cutter jaw for use with the embodiment of FIG. 4.
Figure 10:
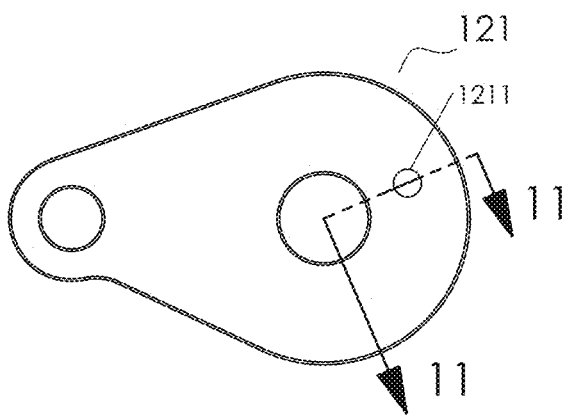
FIG. 10 depicts a top plane view of the cutter jaw of FIG. 9.
Figure 11:
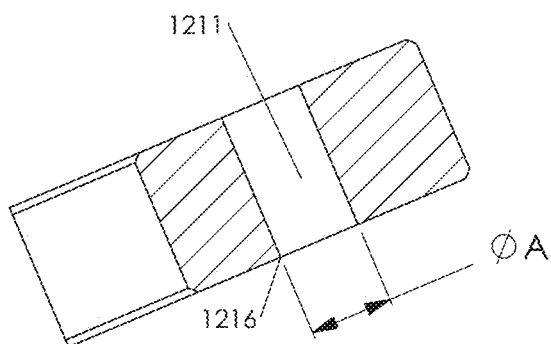
FIG. 11 depicts a sectional view of the cutter jaw from FIG. 10, taken along plane 11-11.

FIGS. 9-11 depict one embodiment of a cutter jaw 121 with a generally cylindrical shearing/cutting hole 1211, a jaw pivot hole 1215 and a fulcrum hole 1213. The features of the jaw cutter 131 is similar to those of corresponding jaw cutter 121, so only a single cutter jaw 121 will be described herein. The enlarged section view of FIG. 11 is defined in FIG. 10 through lines 11-11. In the described embodiment, the shearing/cutting hole 1211 comprises a straight cylindrical surface (see ØA in FIG. 11), although a variety of other hole shapes and/or configurations are contemplated and/or disclosed herein.

In various embodiments, a material, implant or other "part" being cut by the interaction between the hole 1211 and it counterpart (on the other cutting jaw) is preferably slightly smaller than the hole 1211, to desirably allow for easy insertion of the part and/or easy removal of the cut pieces. If the hole is significantly larger than the piece intended to be cut (such as 15% larger or more, for example), the part being cut can potentially rotate, slide or otherwise "tip" in the two cutting holes, which can result in a suboptimal cut (i.e., it could result in a non-square, un-perpendicular end to one or both of the cut pieces). In various embodiments, it may desirous for the edge 1216 to remain sharp, so as to initiate a shearing of the material as it is being cut. When the jaws 121 and 131 move in opposite directions around the pivot holes 1212 and 1312 (SEE FIG. 4), the force applied to the material will desirably cause it to shear the material.

Figure 12:
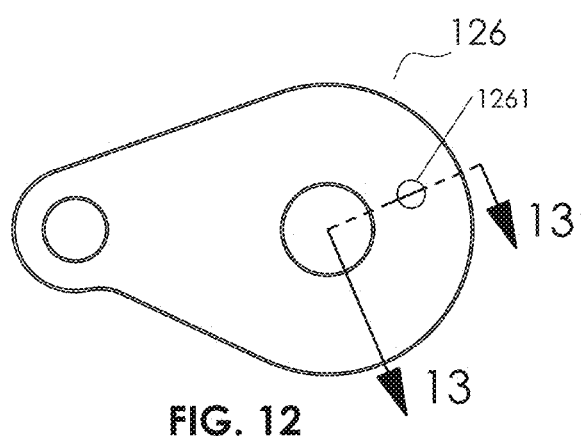
FIG. 12 depicts a top planar view of an alternative embodiment of a cutter jaw.
Figure 13:
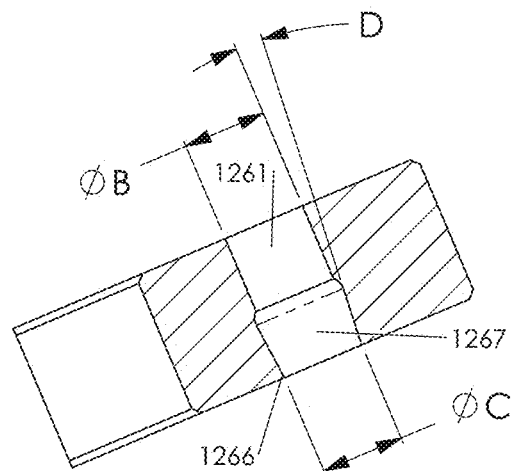
FIG. 13 depicts a sectional view of the cutter jaw from FIG. 12, taken along plane 13-13.

FIGS. 12 and 13 depict another exemplary embodiment 126 of a cutting jaw. In this embodiment, the cutting hole 1267 is not formed in a single straight cylindrical diameter, but is rather formed into a cone shaped hole, followed by a straight cylindrical hole 1261 where the diameters ØB and ØC are similarly sized. The cone angle in this embodiment can be defined by angle D (SEE FIG. 13), and this angle can desirably vary according to the type of material being cut. This embodiment can be particularly well suited for use in cutting materials where a "notch" formed into the surface of the item being cut can facilitate the shearing of the material. In addition, the jaw also includes a straight, cylindrical portion 1261, which can perpendicularly support the material being cut. Desirably, the sharp edge 1266 can form a notch in the material being cut. Should the jaw cutting edges become dull and/or unsharpenable (i.e., from repeated resharpening operations), the cutting jaws can easily be replaced by removing the nuts 123, 124 and 125 from the shafts 133, 134 and 135, respectively.

Figure 14:
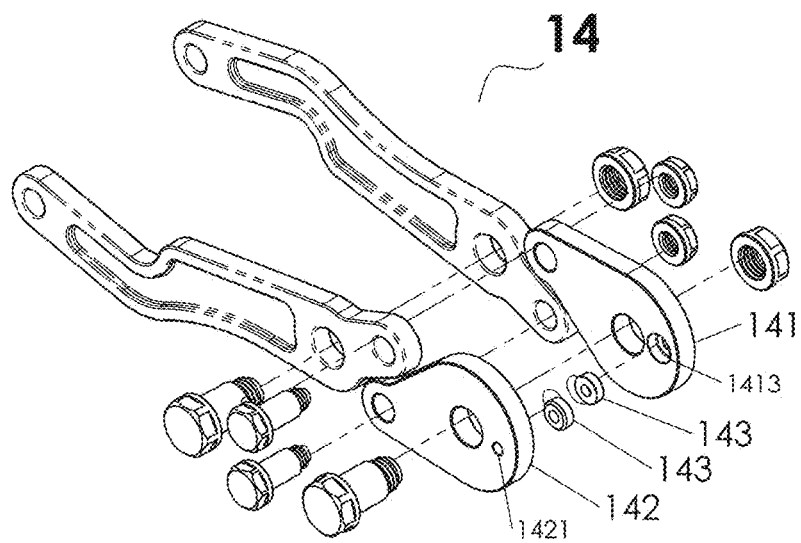
FIG. 14 depicts an exploded view of another alternative embodiment of a cutter sub-assembly.
Figure 15:
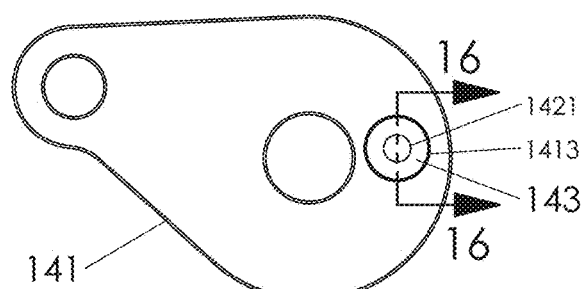
FIG. 15 depicts a top planar view of a sub-assembly of a cutter jaw and insert from the embodiment of FIG. 14.
Figure 16:
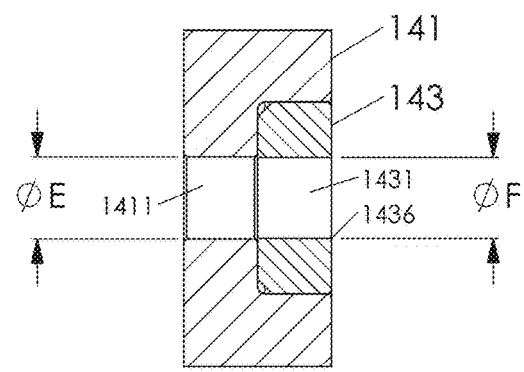
FIG. 16 depicts a sectional view of the cutter jaw sub-assembly from FIG. 15, taken along plane 16-16.

FIGS. 14-16 depict another additional embodiment of the cutter jaws, where the cutter jaws 141 and 142 contain a replaceable cutting element or insert within a counter-bore 1413 (of 141). Only one cutter jaw 141 will only be described herein, as the features of 142 can be similar and/or a mirror image of those of 141. Inside the counter-bore 1413 is placed a cutting/shearing insert 143. The insert 143 can be made of the same material as the cutter jaw 141 or it can be made from harder material, such as silicon carbide. The insert 143 can also be coated with a surface treatment like titanium nitride (TiN) or other surface treatments to strengthen the cutting material or to prevent surface deposits, even galling, from occurring. Those skilled in the art should understand that the counter-bore 1413 would not necessarily have to be round in shape, but could be almost any shape, as long as the cutting insert 143 desirably mates with it. As shown in FIG. 16, the diameters 1411 (ØE) and 1431 (ØF) can be similar in size to hold the material being cut in a perpendicular manner (which may be similar to cutter jaw 121).

Figure 17:
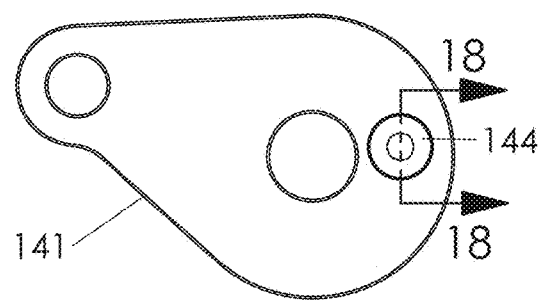
FIG. 17 depicts a top planar view of another alternative embodiment of a sub-assembly of a cutter jaw, comprising a cutter jaw and insert.
Figure 18:
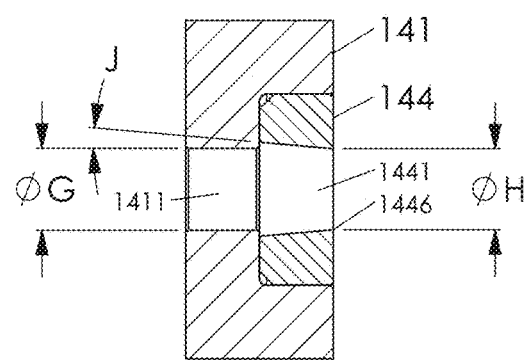
FIG. 18 depicts a sectional view of the cutter jaw sub-assembly from FIG. 17, taken along plane 18-18.
Figure 19:
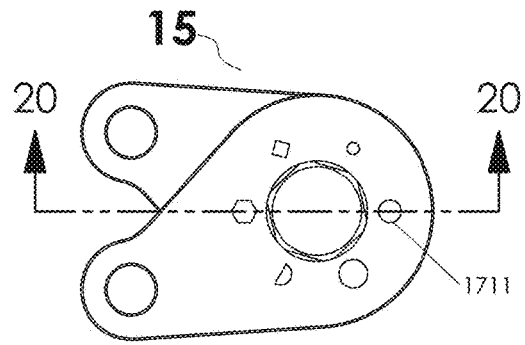
FIG. 19 depicts a top planar view of a sub-assembly of another alternative embodiment of cutter jaws.
Figure 21:
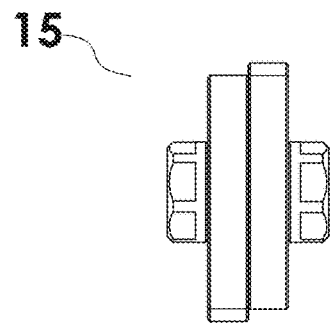
FIG. 21 depicts a right-side planar view of a sub-assembly of another alternative embodiment of a cutter jaw assembly.
Figure 20:
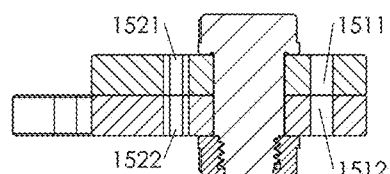
FIG. 20 depicts a sectional view of the cutter jaw sub-assembly from FIG. 19, taken along plane 20-20.
Figure 22:
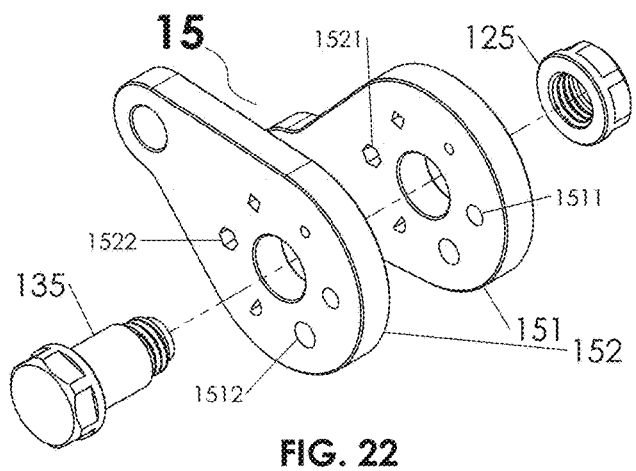
FIG. 22 depicts an exploded view of the sub-assembly from FIG. 19.

FIGS. 17 and 18 depict another additional embodiment of the cutter jaws, where the cutter jaw 141 has a cutting insert 144 having a conical hole 1441. In this embodiment, the cone angle is defined by angle J (SEE FIG. 18), and this angle can vary depending upon the shape and/or type of material being cut. In addition, a straight cylindrical hole 1411 (ØG) and the cutting edge 1446 diameter (ØH) can be similarly sized, as was described earlier for cutting jaw 126. Should the jaw cutting insert edges 1436 and 1446 become dull, the cutting jaw inserts can easily be replaced by removing the nuts 123, 124 and 125 from the shafts 133, 134 and 135, respectively. In various alternative embodiments, the cutting insert could comprise a non-circular outer surface (not shown), such as an oval, triangular, square, pentagonal and/or hexagonal outer surface, which could fit into a corresponding oval, triangular, square, pentagonal, hexagonal and/or polygonal hole in the cutting jaw. Such an arrangement could allow the insert to be removed from the cutting jaw and reinserted in a different orientation, thereby refreshing and/or presenting a sharp cutting surface towards the material to be cut.

FIGS. 19-22 depict an additional alternative embodiment 15 of a cutting jaw, where the cutting jaws 151 and 152 have multiple cutting features comprising multiple shapes. In this embodiment, straight holes 1511 and 1512 are shown with multiple holes formed into each of the cutting jaws, with one set of corresponding holes being hexagonal in cross section 1521 and 1522 (SEE FIGS. 20 and 22). Those skilled in the art should understand that the shapes of the holes could vary, including square, oval, hexagonal, round and/or any geometric shape that matches and/or substantially corresponds to the item being cut. The holes could be of varying sizes and/or shapes, including holes of one size and varying shapes as well as holes of one shape and varying sizes (or various combinations thereof). Moreover, one or more of the holes could be positioned closer into and/or further away from the jaw pivot hole of the cutting jaw, so as to increase and/or decrease the amount of force multiplication eventually applied to cutting actions in such holes (i.e., smaller holes could be positioned further from the pivot hole while larger holes could be positioned closer to the pivot hole—thereby increasing the force multiplication for cutting of the larger diameter objects as compared to cutting of the smaller diameter objects).

Figure 23:
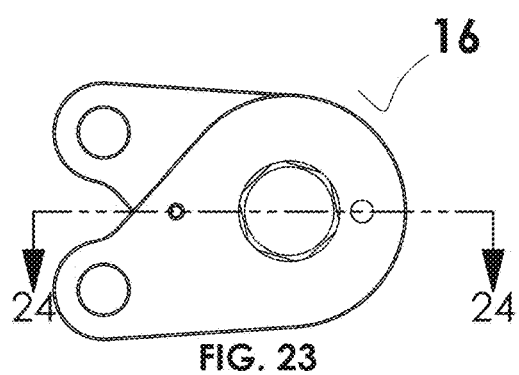
FIG. 23 depicts a top planar view of a sub-assembly of another alternative embodiment of a cutter jaw assembly.
Figure 24:
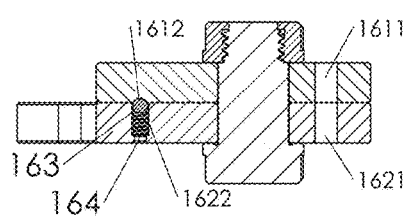
FIG. 24 depicts a sectional view of the cutter jaw sub-assembly from FIG. 23, taken along plane 24-24.
Figure 25:
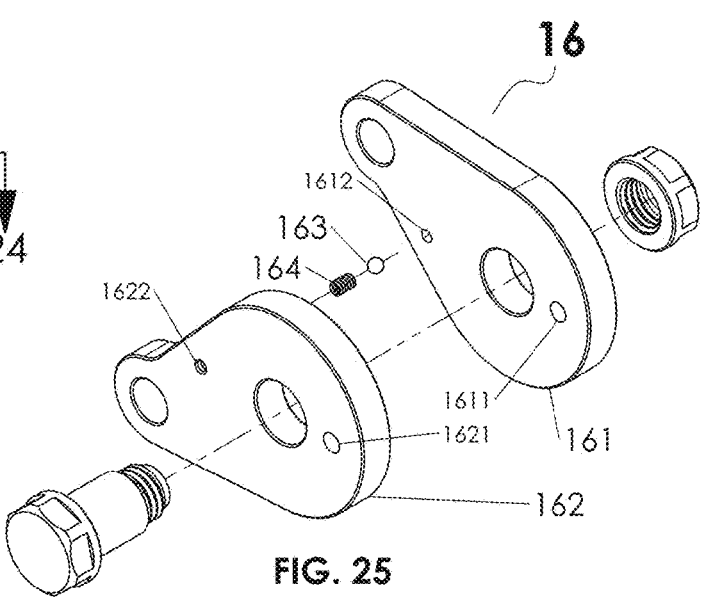
FIG. 25 depicts an exploded view of the sub-assembly from FIG. 23.

FIGS. 23 through 25 depict another alternative embodiment of a cutter jaw assembly 16, in which a spring 164 and a ball 163 can be placed at least partially within a counterbore 1622 of jaw 162. The spring is desirably compressed when the jaws 161 and 162 are assembled, and the spring desirably applies a load to a ball 163 to push the ball into a mating surface or depression 1612 of cutting jaw 161. When the handgrips are rotated to the starting position, the spring 164 will desirably push the ball 163 into the mating surface 1612, which desirably creates a tactile and/or audible feedback to inform the user that the holes 1611 and 1621 are aligned and ready for insertion of the material to be cut. When the handles are rotated during a cutting action, the curved surface of the ball will desirable allow the ball to travel up and out of the depression 1612, thereby allowing motion of the cutting jaws in the normal manner. Those skilled in the art should understand that this ball and spring action could be placed in other locations of the cutting device, such as, but not limited to, between the arm 102 and lever 120 or between the levers 120 and 130, and produce the same or a similar tactile and/or audible feedback to the user.

FIGS. 26-31 depict another alternative embodiment of a cutting device 2, where the "open" position of the cutter can be defined by a physical stop or lever. As best seen in the enlarged, exploded view of FIG. 27, the cutting device can include a shaft 202 and lever 201 that replace the shaft 105 and lever 130 of the embodiment of FIGS. 3 and 4. The shaft 202 can include a polygon shaped male boss 2026 that fits into a polygon shaped female counter-bore 2011 on lever 201. The polygon shapes 2011 and 2026 are configured and arranged in such a manner so as to desirably hold the stop assembly in a proper position, yet allow the lever arms and associated components to move and/or rotate in their desired manner. In this embodiment, when the nut 105 is tightened, it desirably does not prevent the main lever arm 112 (see FIG. 3) from rotating on the shaft 202. The hole 2052 (SEE FIG. 30) of the stop arm 205 can be placed over the shaft diameter 2029 of the shaft 202 and is secured by nut 206. Prior to placing the nut 206 and the stop arm 205 on the shaft 202, the stop pin 203 and torsion spring 204 can be placed into position on the shaft 202. The stop pin 203 is inserted into the hole 2022 of the shaft 202. When the torsion spring 204 is placed over the shaft diameter 2029, the small foot 2042 of the torsion spring 204 can be placed into the hole 2021 of the shaft. When the stop arm 205 is lowered into place onto the shaft 202, the long leg 2041 of the torsion spring 204 can be placed against the flat surface 2056 of the stop arm. This arrangement causes the torsion spring 204 to apply pressure in an opposite direction of the radial arrow C (see FIG. 29), and desirably keeps the surface 2058 of the stop arm 205 firmly against the shaft diameter 1041 of the shaft 104. When the cutting jaws are in an open or starting position, the diameter 1041 of shaft 104 will desirably be nested into radius 2057 of the stop arm 205. Once assembled, the nut 206 can optionally be friction fit, bonded or welded to the shaft 202 to prevent accidental disassembly. This securing can be done to the various features 2063 and 2064 of the nut and 2023 and 2024 of the shaft 204.

Another significant feature of various cutting device embodiments constructed in accordance with the teachings of the present invention is an ability to "switch" or change the location of the cutting mechanism from between the handles (SEE FIGS. 1 and 2) to extending outward and away from the handles (see FIGS. 38 and 39). This arrangement can significantly improve the versatility of the cutting device, in that the extended position (FIG. 39) allows a user the ability to be further away from the cutting mechanism, such as where the item to be cut is held or loaded by an assistant, the item is located within a surgical wound or other "tight" location or where the item might potentially flex, shatter or undesirably fracture when being cut (and thus may desirably be held "away" from an individual). For example, a surgeon may prefer the extended position where a surgical assistant is loading the object being cut from another side of a surgical table, or is otherwise not adjacent to the surgeon. In the alternative configuration, the device can be quickly and conveniently shifted to a compacted position (FIG. 38), in which the cutting mechanism is positioned between the handles, which greatly reduces the size and "footprint" of the device, allowing the cutting mechanism to be nearer to the user, which can allow the item to be cut to be held by the user and/or against the user's body). The reduced footprint of the compacted position can also facilitate cutting device storage, cleaning and/or sterilization (i.e., it can fit into a smaller steam autoclave, if desired), and may also reduce space requirements on a surgical table or other areas.

Figure 67D:
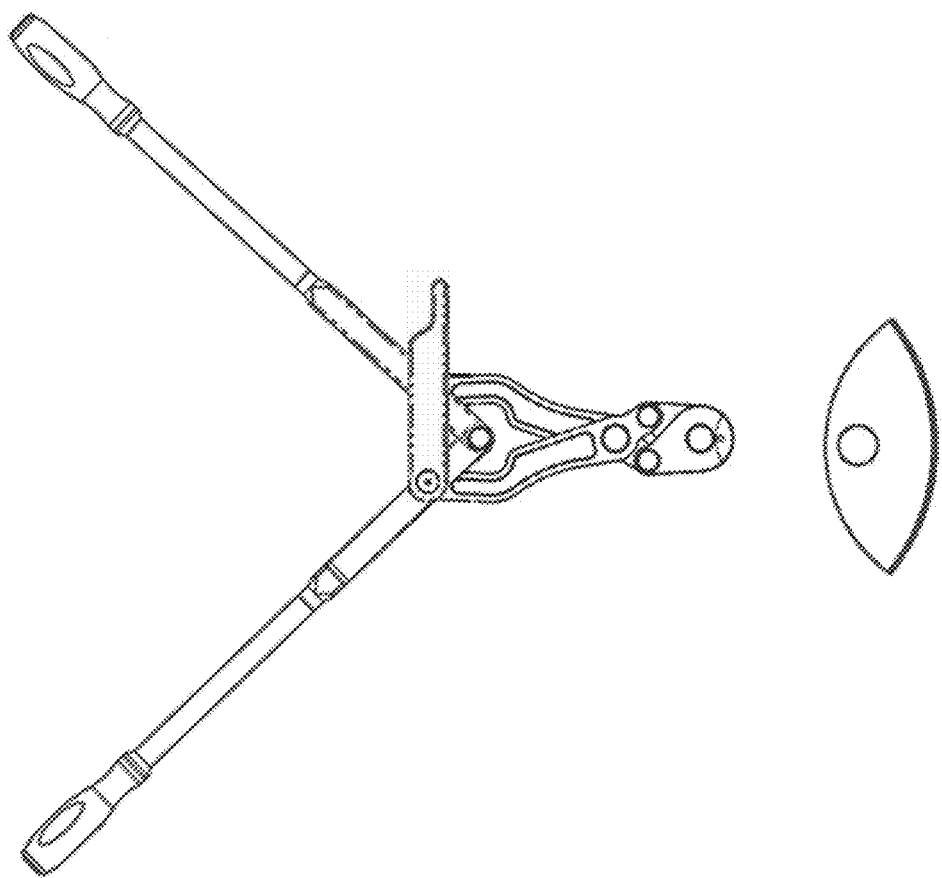
FIG. 67D depicts a side view of the cutting device of FIG. 67A in a fourth handle position.

In various embodiments, because the distances L1 through L6 remain essentially the same in the extended and compacted positions, the mechanical advantages and cutting forces produced by manipulation of the handles can remain essentially the same in either orientation. For some embodiments, this can be accomplished by simply moving the handles to the opposing orientation, while in other embodiments it may be necessary to operate a latch, detent or other securing mechanism to allow assumption for the opposing configuration. For example, in the embodiment of FIG. 26, if the user wants to "flip" the handle assemblies 10 and 11 to the opposite side (so that the cutter subassembly 12 is no longer between the handle assemblies 10 and 11 but rather outside of them—SEE FIGS. 38 and 39), the user can rotate the stop arm 205 in the direction C (shown in FIG. 29) till the stop pin 203 contacts the stop face 2054 of the stop arm 205. The handle assemblies can then be rotated to an opposing orientation, as shown in FIGS. 38 and 39, with the bent, curved, indented or offset portions 1204 and 1304 of the lever arms 120 and 130 accommodating distal ends of the main arm assemblies 10 and 11 (which in various alternative embodiments could include a bent portion in one or both of the lever arms). The shaft diameter 1041 will slide toward the end of the stop arm on surface 2059 of the stop arm 205. When the rotational movement of the handle assemblies 10 and 11 reaches the halfway mark of the rotational distance the shaft diameter 1041 will retreat down the surface 2059 of the stop arm 205 where it will eventually drop back into the pocket formed by surfaces 2057 and 2058. This arrangement may be a "fourth position" for the first and second levers, depicted in FIG. 67D.

When using this embodiment of the cutting device, a user can set the starting or open position of the cutting holes in the jaws by extending the handles open until the shaft diameter 1041 comes into contact with surface 2057. The cutter can then be utilized as normal. To switch back to the "compacted" position (i.e., to have the cutter assembly 12 inside the handles assemblies 10 and 11), the user need merely repeat the above-listed steps in the opposite direction. Because of the placement of stop pin 203 between stop surfaces 2054 and 2055, the stop arm can be useable in either position.

In the embodiment shown in FIGS. 23 through 25, the arrangement of the ball and spring detent assembly can desirably allow the user to simply rotate the handles to the desired extended and/or compacted orientation, with the ball pushed into the mating surface to create a tactile and/or audible feedback to inform the user that the holes are aligned and ready for insertion of the material to be cut. When the handles are rotated during a cutting action (in either of the listed orientations), the curved surface of the ball will desirable allow the ball to travel up and out of the depression, thereby allowing motion of the cutting jaws in the normal manner.

FIGS. 40 through 47 depict another alternative embodiment of a cutting device 3 constructed in accordance with various teachings of the present invention, wherein the device incorporates removable handgrips 19. Unlike previous embodiments where the handgrip forms an integral portion of each handle, the handles 101 and 111 of the cutting device 3 include male posts 171 at a proximal end of each handle, with the male posts engaged with corresponding handgrips to form handle assemblies 19. FIG. 41 depicts an enlarged view of the male post 171, each of which comprises: a pair of symmetrical flat faces 1718 (one of which is hidden in FIG. 41), two additional symmetrical flat surfaces 1714 (one of which is hidden in FIG. 41), two diameters 1711 and 1712, a conical surface 1713 and a groove comprising diameter 1717 and walls 1715 and 1716. As best seen in FIGS. 43 and 45, the removable hand grip 19 has a body core 192, a grip 193, a release knob 195, a locking pin 196, a spring 197 and a female connector 194. Inside the female connector 194 there are two female symmetrical flat surfaces 1941 (one of which is hidden in FIG. 45), two additional female symmetrical flat surfaces 1944 and a cylindrical surface 1941. The flat surfaces 1714 and 1718 and diameters 1711 and 1712 desirably mate with the female flat surfaces 1944 and 1948, and cylindrical surface 1941, respectively, when the handgrip 19 is attached to the male post 171. The afore-mentioned flat surfaces desirably orientate and prevent rotation of the removable handgrips 19 on the male posts 171. As shown in FIGS. 43, 44 and 45 there can be various additional features to lock the handgrip 19 in place on the male post 171, if desired. A spring 197 can be placed on the locking pin 196 and passed through hole 1945, counter-bore 1947, hole 1946 and counter-bore 1942. The diameter 1964 of the locking pin 196 can then be inserted into hole 1951 of the release knob 195. The locking pin 196 and knob 195 can be joined together through any manner or processes which could include, but not limited to welding, interference fits and/or bonding. When this embodiment of the assembly is complete, the spring will desirably apply pressure to faces 1963 and 1943, moving face 1952 against counter-bore 1942. When the removable handgrip 19 is attached to the male post 171, the conical surface 1715 (SEE FIG. 43) of the male post 171 can contact the diameter 1961 of the locking pin 196, forcing it to travel along and up the conical surface 1715, thereby compressing the spring 197. The removable handgrip 19 can continue to advance onto the male post 171 until the locking pin diameter 1961 enters the area of the groove 1717. The spring pressure of the spring 197 will then cause the locking pin assembly to drop into the groove 1717, and the walls 1715 and 1716 of groove 1717 can prevent accidental dislodging of the removable handle 19. To disengage the removable handle 19 from the male post 171, a user can simply pull on the knob 195 of the locking pin assembly, which retracts the diameter 1961 from the groove 1717 and then allows for disengagement of the removable handle 19 from the male post 171. Those skilled in the art should understand that the body of the handgrip does not have to made from different components 192, 193 and 194 but can be made from a single component or combination of two or more components, if desired. It should also be understood that the spring 197 need not be a wave spring as shown, but other types of springs such as compression or disc or other types may be made from other flexible materials such as rubber.

Figure 48:
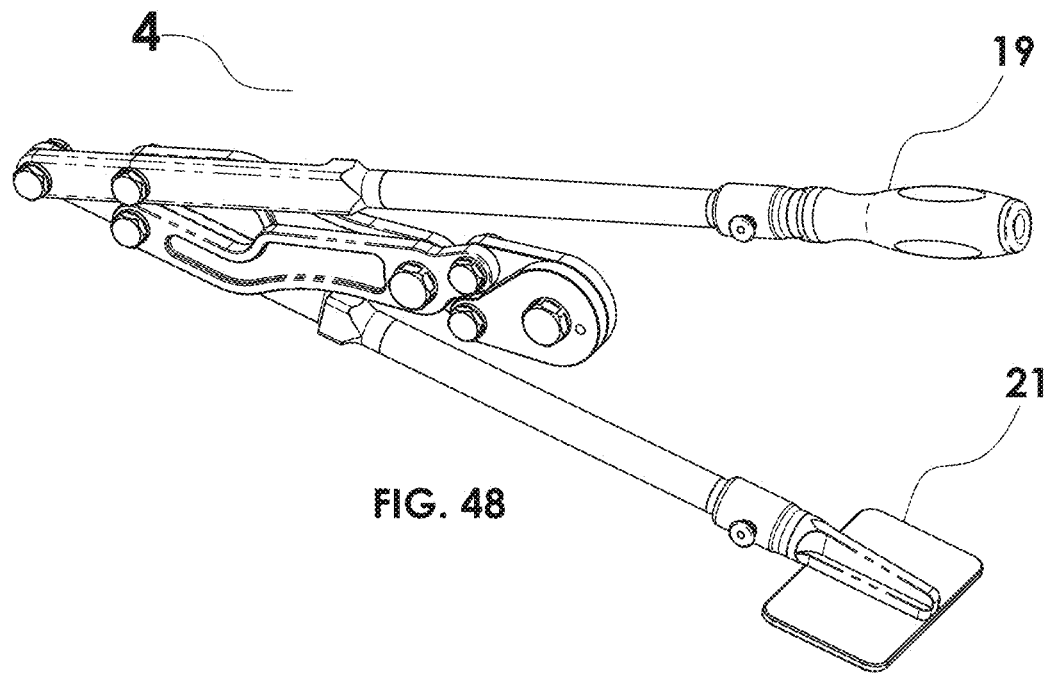
FIG. 48 depicts a perspective view of another alternative embodiment of a cutting tool incorporating various features of the present invention, with a single removable handgrip and a removable foot.
Figure 49:
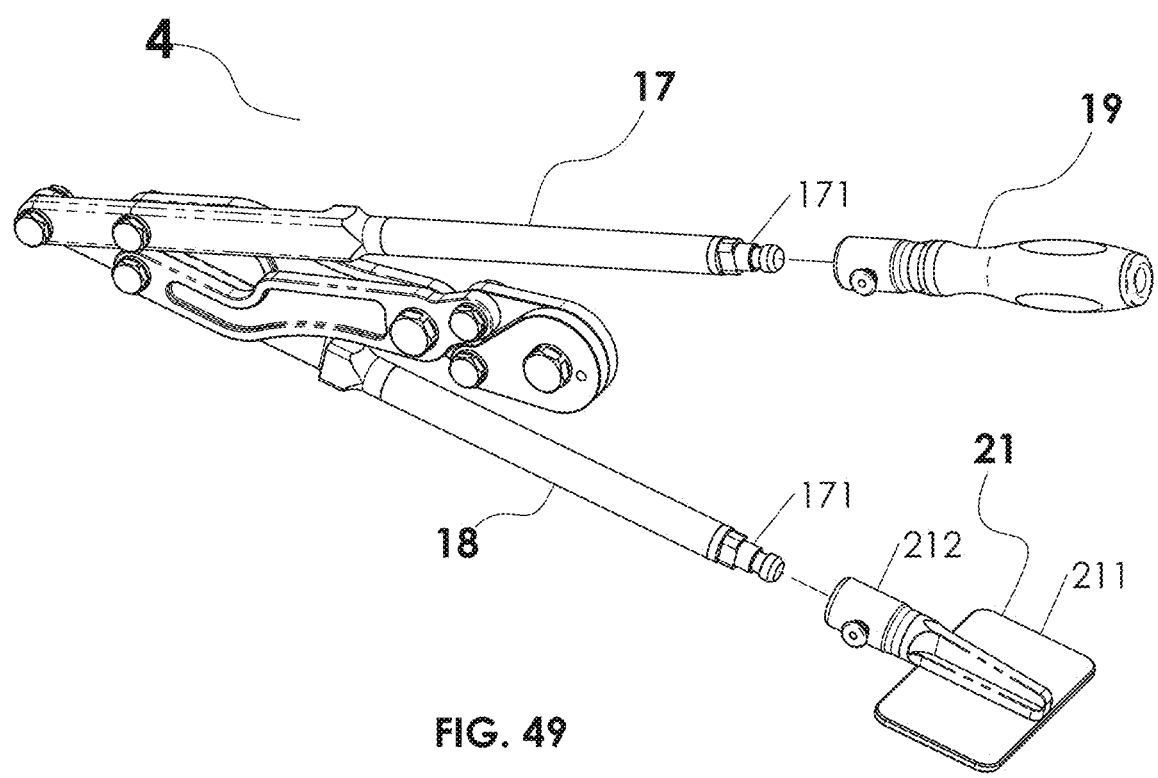
FIG. 49 depicts a semi-exploded perspective view of the embodiment of FIG. 48.

FIGS. 48 and 49 depict another alternative embodiment of a cutting device 4 constructed in accordance with various of the teaching herein, in which the cutter has a removable handgrip 19 and a removable stabilizer 21. The removable stabilizer 21 can be attached and utilized to "convert" the handheld cutter to use as a tabletop cutter for use on a flat surface or the cutter can be placed against a location on the user's body, like a hip (SEE FIG. 56), while two hands are placed in the handgrip 19 area and the hip to the stabilizer 21. The female connector 212 depicted herein can be similar to the female connector 194 described previously, with one potential difference being that it may be attached to a flat foot 211 instead of to handgrip components 192 and 193. Those of ordinary skill in the art should understand that another alternative embodiment could have an integrally formed handgrip 19 and/or flat foot 21, as well as the removable components shown in cutter 8 (see FIG. 55).

Figure 50:
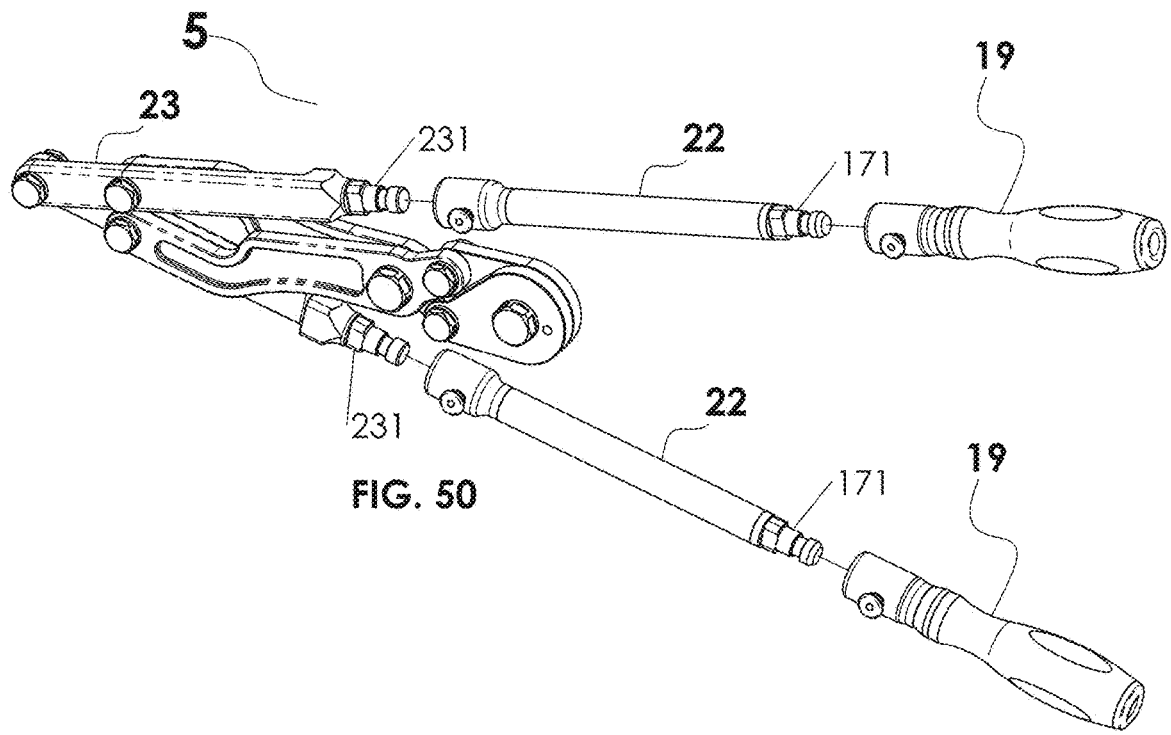
FIG. 50 depicts a semi-exploded perspective view of another alternative embodiment of a cutting tool incorporating various features of the present invention, with removable handgrips and removable handles.

FIG. 50 depict another alternative embodiment of a cutting device 5 constructed in accordance with various of the teaching herein, in which the cutter can include removable handgrips 19 and removable handles 22. In this embodiment, the cutter assembly 23 has male posts 231 attached to accept the removable handles 22, although a wide variety of alternative fastening arrangements are contemplated herein. Though not shown, it should be understood by those skilled in the art that various lengths of the handles 22 can be made and/or included in a kit (including kits with multiple handles of varying lengths) to match the cutting force needed for the particular material being cut.

Figure 51:
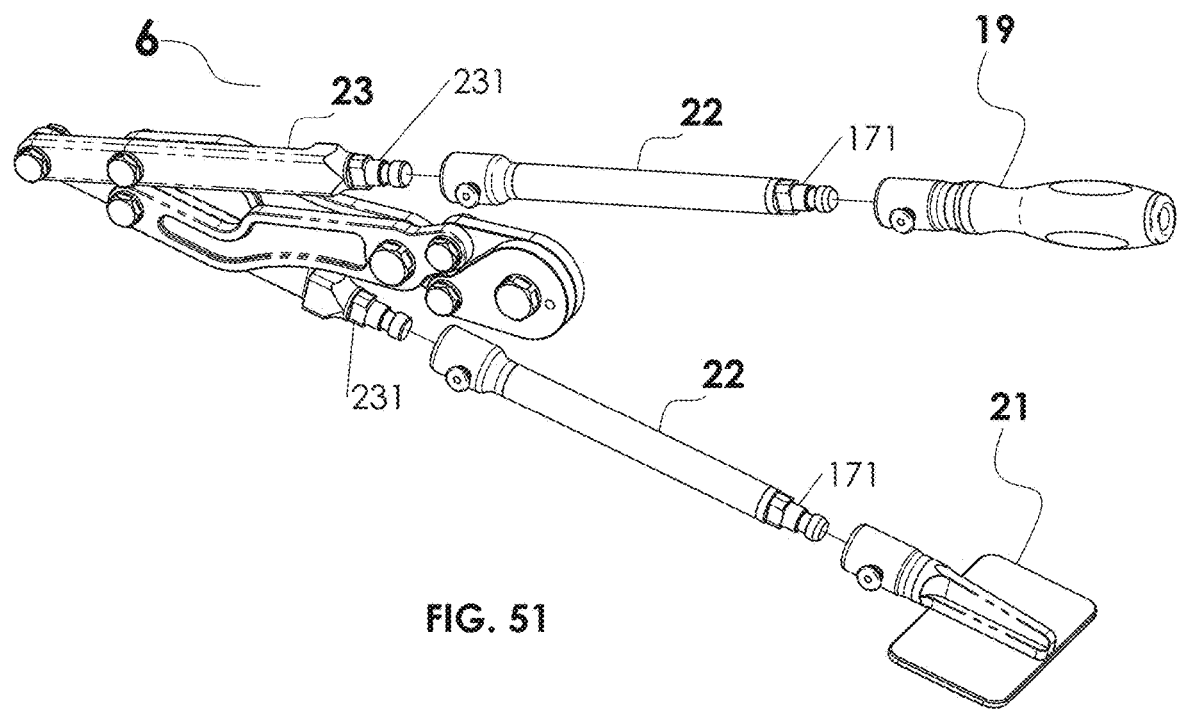
FIG. 51 depicts a semi-exploded perspective view of another alternative embodiment of a cutting tool incorporating various features of the present invention, with a single removable handgrip, a removable foot and removable handles.

FIG. 51 depicts another alternative embodiment of a cutting device 6 constructed in accordance with various of the teaching herein, in which the cutter incorporates a removable handgrip 19, removable handles 22 and a removable stabilizer 21.

Figure 52:
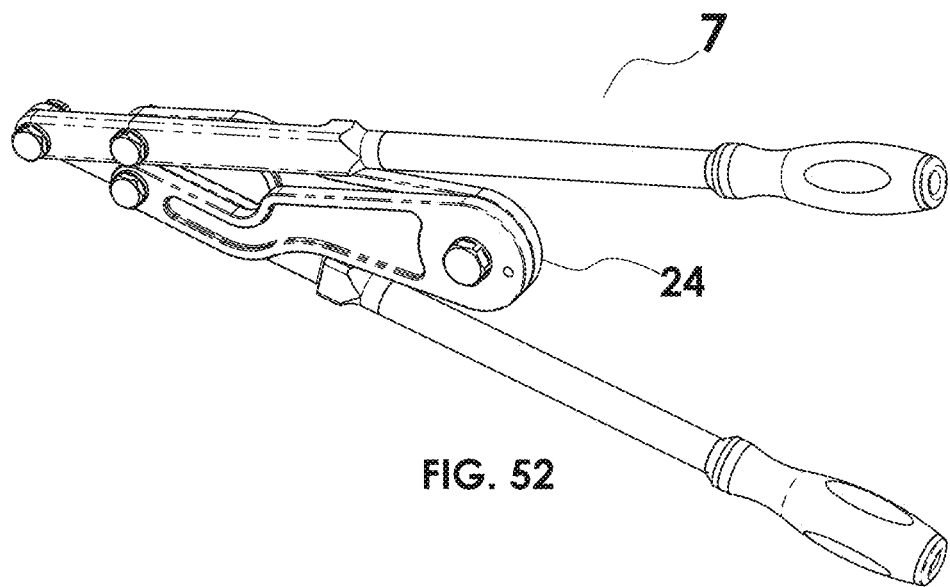
FIG. 52 depicts a perspective view of another alternative embodiment of a cutting tool incorporating various features of the present invention, with an elongated cutter jaw.
Figure 53:
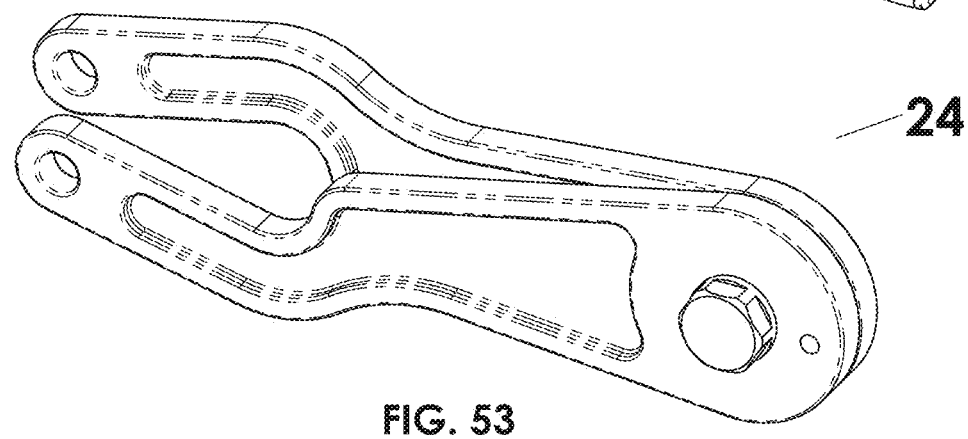
FIG. 53 depicts a perspective view of the elongated cutter jaw sub-assembly of FIG. 52.
Figure 54:
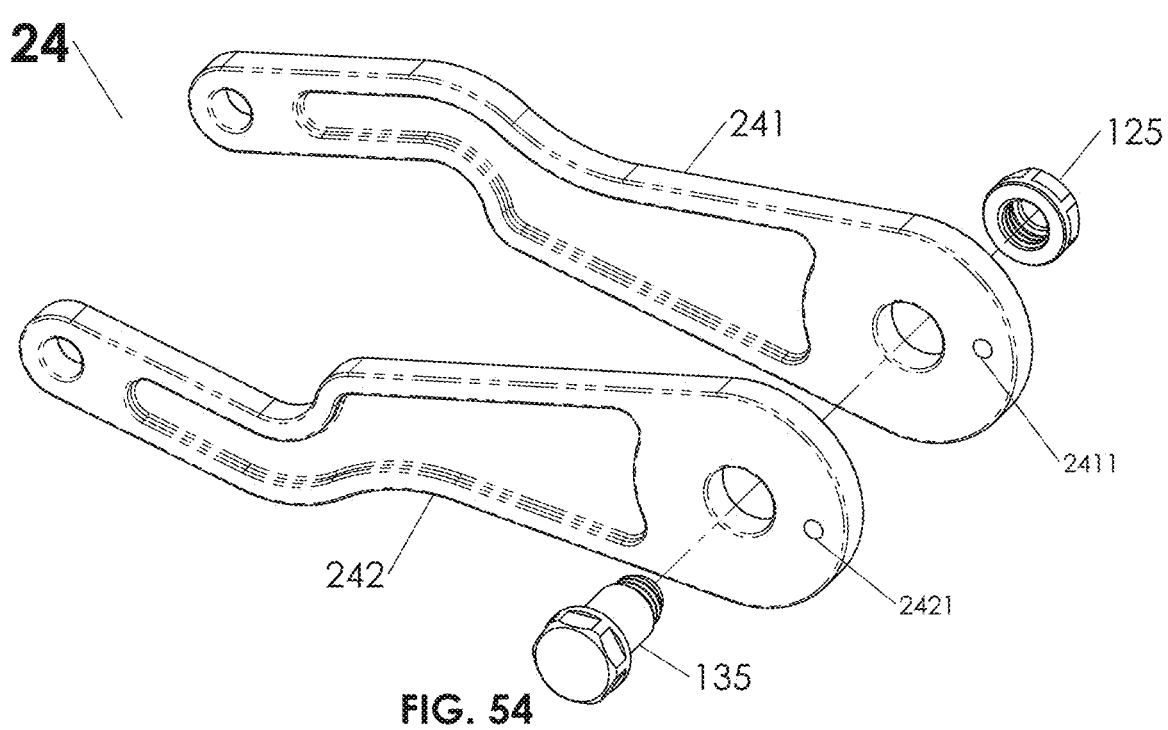
FIG. 54 depicts an exploded perspective view of the elongated cutter jaw sub-assembly of FIG. 53.

FIGS. 52 through 54 depict another alternative embodiment of a cutting device 7 constructed in accordance with various of the teaching herein, in which the cutter assembly 24 includes only a single set of supplemental lever arms, which may be particularly useful in cutting softer material of other materials where application of a lower mechanical advantage might be preferred. FIG. 53 shows an enlarged perspective view of the single lever arm cutter assembly 24. FIG. 54 depicts an exploded perspective view of the single lever arm cutter assembly 24, in which the two single cutters 241 and 242 include cutting holes 2411 and 2412 which pivot about a bolt 135 and nut 125.

FIGS. 55, 56A, 56B and 56C depict various alternative embodiments of a cutting device constructed in accordance with various of the teaching herein which can incorporate a variety of contact surfaces, such as flat 21, curved 28 or angled 29 stabilizer surfaces. FIG. 55 depicts one exemplary embodiment of a cutting device 8 with a removable flat stabilizer assembly 21 that can be utilized when the cutting device is resting on a flat, or planar, surface. The flat stabilizer 21 desirably orients the invention so that the cutting assembly 12 is perpendicular to the afore mentioned planar surface. In various embodiments, the flat stabilizer can provide support to maintain the cutting device vertically for use, and/or may "steady" the cutting device during use. Those of ordinary skill in the art should understand that an integral clamping system of this type, or an external clamp (such as, but not limited to, a "C-Clamp") could be used in a variety of ways to further stabilize the invention on various surfaces which might not be limited to planar surfaces. One skilled in the art should also comprehend that the flat stabilizer assembly 21 described herein could alternatively be formed integrally with the cutter arm, and not be easily removable.

FIG. 56A shows how the embodiment of a cutting device 8 can be used in a vertical position, where the flat plate stabilizer 21 may be placed against the user's body or some other vertical surface. FIG. 56B depicts a radial (i.e., curved) stabilizer assembly 28 and FIG. 56C depicts an angled stabilizer assembly 29. Those of ordinary skill in the art should contemplate that various other shapes and/or combinations of flat, curved and angled stabilizer assemblies are possible, without deviating from the from the spirit or essential character of the plate assembly.

Figure 57:
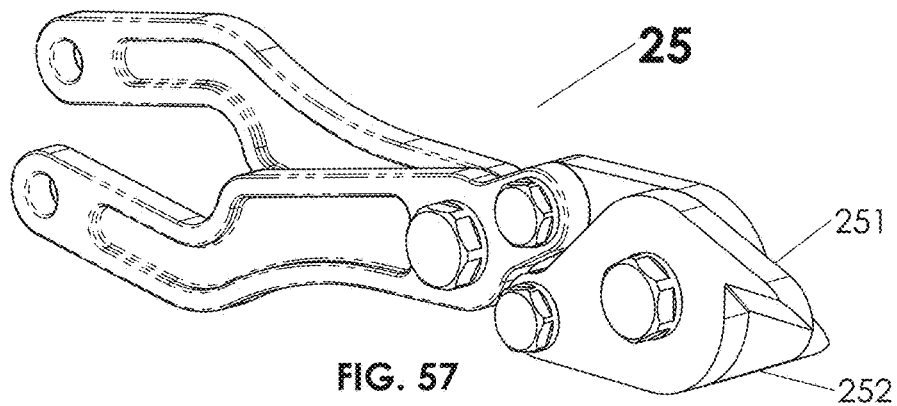
FIG. 57 depicts a perspective view of another alternative embodiment of a cutting tool incorporating various features of the present invention of the invention, with a slicing cutter jaw assembly.

FIG. 57 depicts a perspective view of another alternative embodiments of a cutting device constructed in accordance with various of the teaching herein, wherein the cutting device 25 incorporates a slicing cutter jaw. The slicing cutter jaws 251 and 252 desirably utilizes a slicing action in addition to the mechanical advantages described herein when cutting sheet material.

Figure 58:
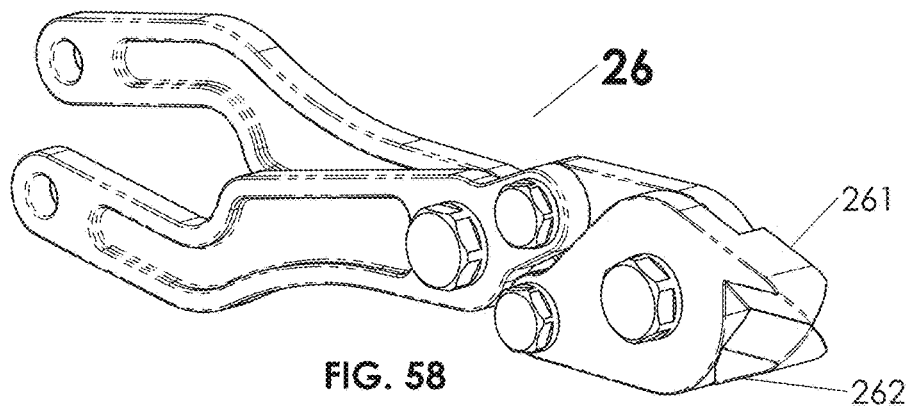
FIG. 58 depicts a perspective view of another alternative embodiment of a cutting tool incorporating various features of the present invention, with a pinching cutter jaw assembly.

FIG. 58 depicts a perspective view of another alternative embodiments of a cutting device constructed in accordance with various of the teaching herein, wherein the cutting device 26 incorporates a pinching cutter jaw. The pinching cutter jaws 251 and 252 desirably utilizes a pinching action in addition to the mechanical advantages described herein, and further allows for an open-ended jaw.

Figure 59:
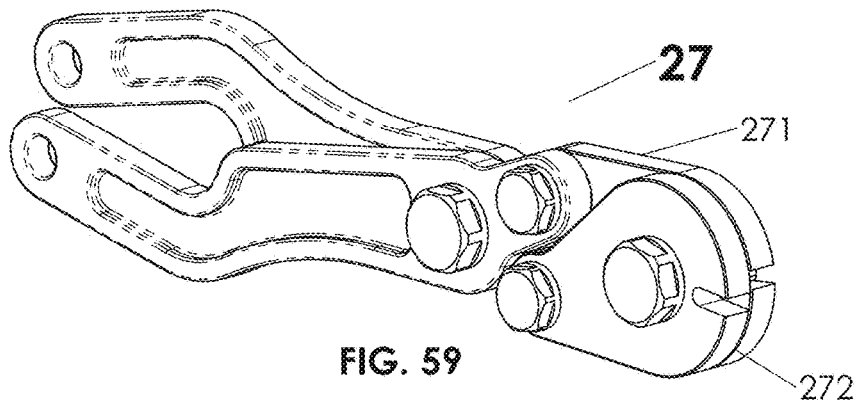
FIG. 59 depicts a perspective view of another alternative embodiment of a cutting tool incorporating various features of the present invention, with a set of open shearing jaws.

FIG. 59 depicts a perspective view of another alternative embodiments of a cutting device constructed in accordance with various of the teaching herein, wherein the cutting device 27 incorporates a set of open shearing jaws. The open-ended jaws 271 and 272 desirably utilizes a shearing action in addition to the mechanical advantages described herein, and further allows for an open ended shearing jaw.

Figure 60:
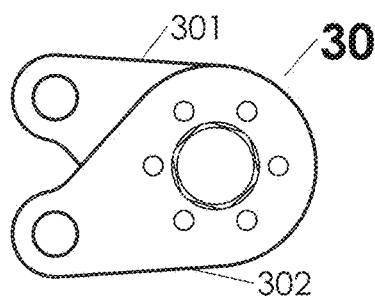
FIG. 60 depicts a top planar view of an alternative embodiment of a cutting jaw sub-assembly, with the jaws in an open position.
Figure 61:
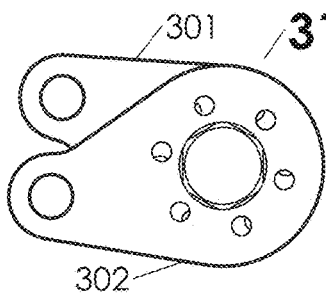
FIG. 61 depicts a top planar view of another alternative embodiment of a cutting jaw sub-assembly, with the jaws in a cutting position.

FIG. 60 depicts another alternative embodiment of a cutting device 30 constructed in accordance with various of the teaching herein embodiment 30 constructed in accordance with various of the teaching herein, wherein the cutting tip includes a series of multiple cutting holes, which can be of the same and/or different diameters, in the cutting jaws 301 and 302. This feature gives the user additional cutting options when one set of cutting holes becomes dull after prolong use, thus increasing the usable life of the instrument by multiples of the amount of duplicate hole positions, without having to remove and replace the cutting jaws or portions thereof. As shown in FIG. 61, the additional holes can be capable of performing the same or similar cutting actions as a single hole. It should be understood that the various holes could be located at different distances from the fulcrum cutting head fulcrum point (not shown), to allow for differing mechanical advantages and/or different amounts of shearing or cutting action (i.e., degree of hole rotation).

Figure 62:
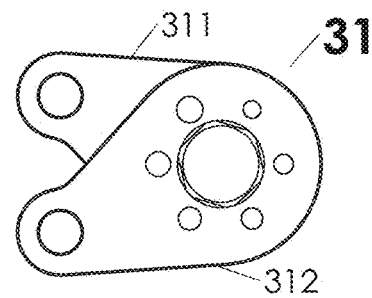
FIG. 62 depicts a top planar view of another alternative embodiment of a cutting jaw sub-assembly, with the jaws in an open position.

FIG. 62 depicts another alternative embodiment of a cutting device 31 constructed in accordance with various of the teaching herein, with the cutting head including multiple cutting holes of differing diameters in the cutting jaws 311 and 312. This feature gives the user the ability to cut various diameters of material while only having one instrument to cut multiple diameters. Those skilled in the art should understand that a combination of embodiments 30 and 31 can be used without departing from the spirit of the invention. It should be understood that the various holes could be located at different distances from the fulcrum cutting head fulcrum point (not shown), to allow for differing mechanical advantages and/or different amounts of shearing or cutting action (i.e., degree of hole rotation).

Figure 63:
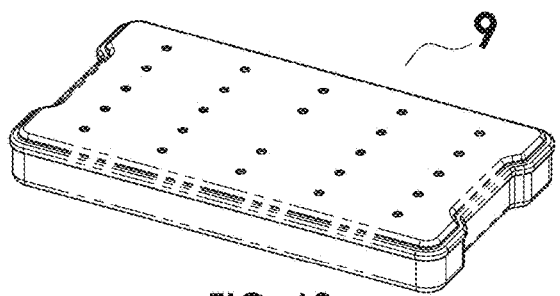
FIGS. 63 through 65 depict various collapsed, exploded and enlarged views of cutting tools and associated components in a tray or kit arrangement.
Figure 64:
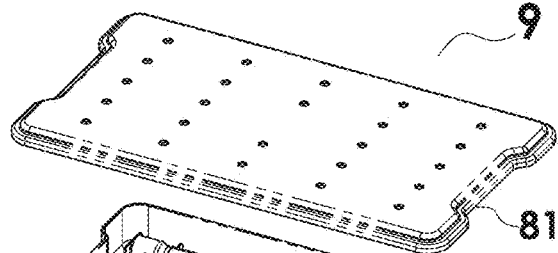
Figure 64:
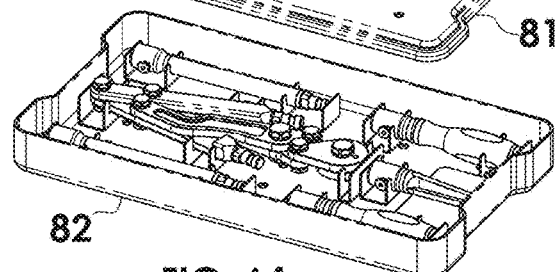
Figure 65:
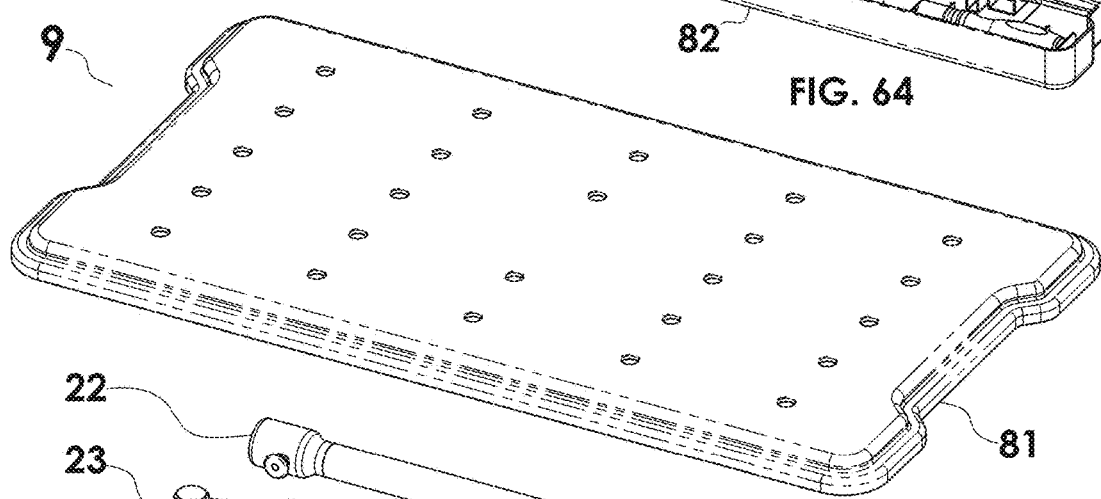
Figure 65:
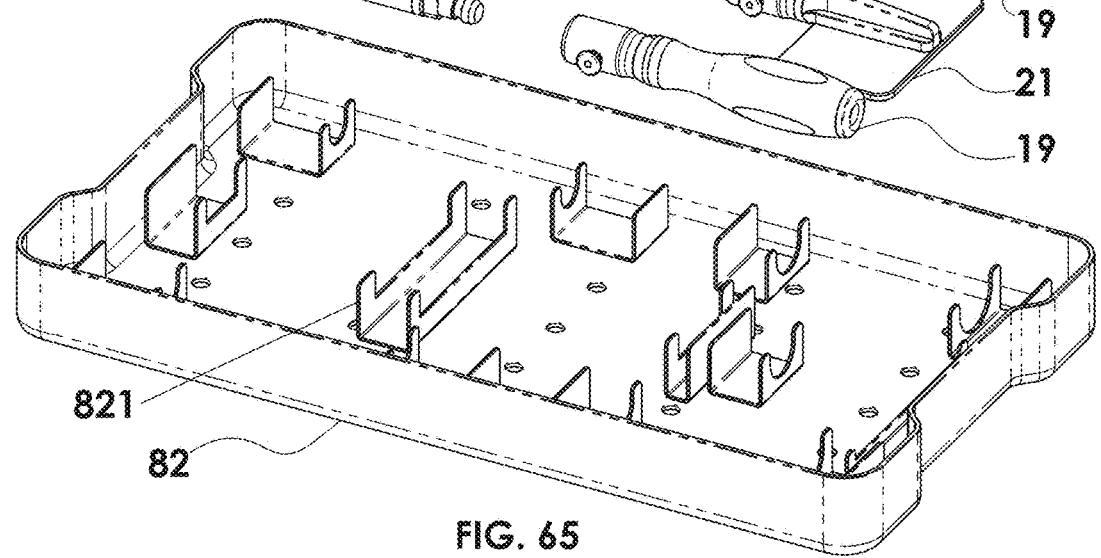
Figure 66A:
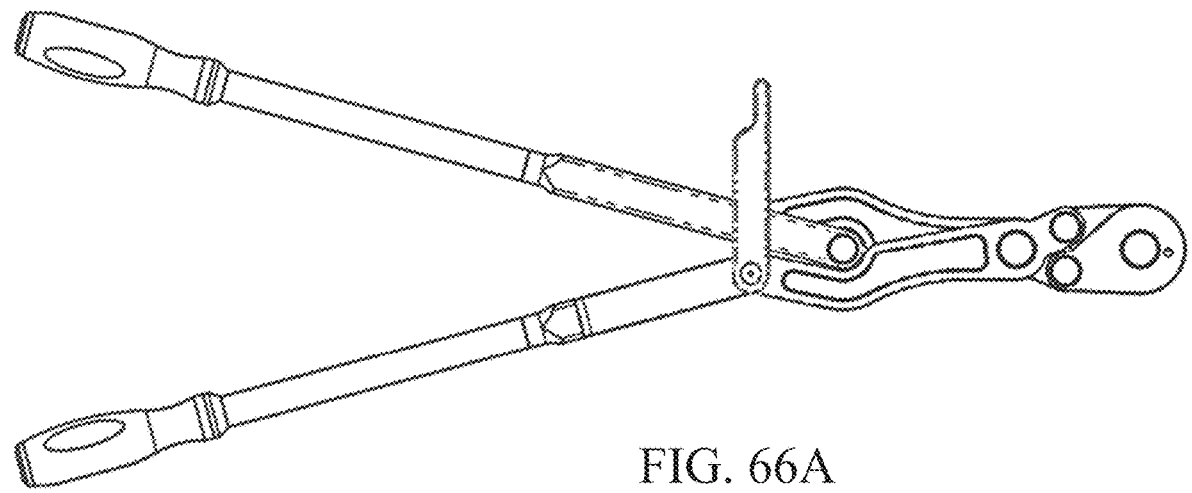
FIG. 66A depicts a side view of one embodiment of a cutting device in a collapsed or finished position.
Figure 66B:
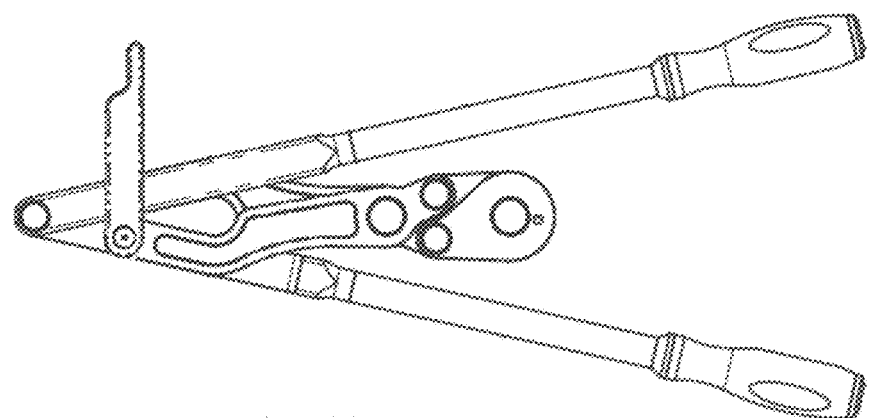
FIG. 66B depicts a side view of the cutting device of FIG. 66A in an open or expanded position.

FIGS. 63-65 depict another exemplary embodiment of a cutting device 9 and associated components constructed in accordance with various of the teaching herein, where the device and associated components can be stored and/or sterilized in a self-contained kit. Though the container top 81, container bottom 82 and supports 821 are shown as a surgical sterilization container, those skilled in the art know that it could also be a container in the form of a toolbox, travel container, with either hard or soft sides or a combination of both.

Alternative Configurations

The various components described herein may be formed in a variety of shapes, sizes and/or configurations. For example, the arms 120 and 130 may be formed in a variety of shapes and configurations, which will desirably facilitate the use of the cutter. Similarly, the various features described herein could include features that are unique to a specific material being cut without departing from the spirit or essential character of the invention.

INCORPORATION BY REFERENCE

The entire disclosure of each of the publications, patent documents, and other references referred to herein is incorporated herein by reference in its entirety for all purposes to the same extent as if each individual source were individually denoted as being incorporated by reference.

EQUIVALENTS

The invention may be embodied in other specific forms without departing from the spirit or essential characteristics thereof. The foregoing embodiments are therefore to be considered in all respects illustrative rather than limiting on the invention described herein. The scope of the invention is thus intended to include all changes that come within the meaning and range of equivalency of the descriptions provided herein.

Many of the aspects and advantages of the present invention may be more clearly understood and appreciated by reference to the accompanying drawings. The accompanying drawings are incorporated herein and form a part of the specification, illustrating embodiments of the present invention and together with the description, disclose the principles of the invention.

Although the foregoing inventions have been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein.

What is claimed is:

1. A surgical cutting tool comprising:
   a first lever set including first and second opposed handle levers in a second-order lever arrangement, each of said first and second opposed handle levers including a handle end and a pivot end;

a second lever set pivotally attached to the first lever set, the second lever set including third and fourth opposed handle levers in a first-order arrangement, each of said third and fourth opposed handle levers including a proximal end and a distal end, the proximal end of the third opposed handle lever pivotally attached to the first opposed handle lever at a location between the handle and pivot ends of the first opposed handle lever and the proximal end of the fourth opposed handle lever pivotally attached to the second opposed handle lever at a location between the handle and pivot ends of the second opposed handle lever;

a third lever set pivotally attached to the second lever set, the third lever set including fifth and sixth opposed handle levers in a second-order arrangement, each of said fifth and sixth opposed handle levers including a proximal end and a distal end, the proximal end of the fifth opposed handle lever pivotally attached to the third opposed handle lever at a location proximate to the distal end of the third opposed handle lever and the proximal end of the sixth opposed handle lever pivotally attached to the fourth opposed handle lever at a location proximate to the distal end of the fourth opposed handle lever;

the fifth opposed handle lever including a first transverse opening extending through the fifth opposed handle lever, the first transverse opening located proximate to a pivot point of the third lever set; and the sixth opposed handle lever including a second transverse opening extending through the sixth opposed handle lever, the second transverse opening located proximate to a pivot point of the third lever set, and a releasable retention element positioned on the first lever set, wherein the first and second transverse openings are substantially aligned for receiving a work piece to be cut therethrough when the first and second opposed handle levers are in a second handle position along a first range of handle motion, the first and second transverse openings rotate substantially out of alignment for cutting the work piece received therethrough when the first and second opposed handle levers are in a first position along the first range of handle motion, and the first and second transverse openings are substantially realigned for receiving a work piece to be cut therethrough when the first and second opposed handle levers are in a fourth handle position along the first range of handle motion, the fourth handle position being at least partially defined by the releasable retention element, the fourth handle position being a different position along the first range of handle motion than the second handle position.

2. The surgical cutting tool of claim 1, wherein the second and third lever sets can be positioned in a collapsed tool configuration with the second and third lever sets located between the first and second opposed handle levers of the first lever set when the first and second opposed handle levers are in the first handle position, and the second and third lever sets can be positioned in an expanded tool configuration with the second and third lever sets extending outward from the first and second opposed handle levers of the first lever set when the first and second opposed handle levers are in the fourth handle position.

3. The surgical cutting tool of claim 1, wherein the fourth opposed lever handle includes an indented portion.

4. The surgical cutting tool of claim 1, wherein the releasable retention element positioned on the second lever set includes a latch, detent or securing mechanism that mechanically engages when the first and second transverse openings are substantially aligned.

5. The surgical cutting tool of claim 1, wherein the fifth opposed lever set include at least one replaceable cutting insert.

6. The surgical cutting tool of claim 5, wherein the at least one replaceable cutting insert comprises a straight cutting insert.

7. The surgical cutting tool of claim 5, wherein the at least one replaceable cutting insert comprises a tapered cutting insert.

8. The surgical cutting tool of claim 1, wherein the first lever set includes a base.

9. The surgical cutting tool of claim 8, wherein the base is removeable from the first lever set.

10. A surgical cutting tool with compound leverage comprising:
a first lever set including first and second opposed handle levers in a second-order lever arrangement, each of said first and second opposed handle levers including a handle end and a pivot end;

a second lever set pivotally attached to the first lever set, the second lever set including third and fourth opposed handle levers in a first order arrangement, each of said third and fourth opposed handle levers including a proximal end and a distal end, the proximal end of the third opposed handle lever pivotally attached to the first opposed handle lever at a location between the handle and pivot ends of the first opposed handle lever and the proximal end of the fourth opposed handle lever pivotally attached to the second opposed handle lever at a location between the handle and pivot ends of the second opposed handle lever;

a third lever set pivotally attached to the second lever set, the third lever set including fifth and sixth opposed handle levers in a first or second-order arrangement, each of said fifth and sixth opposed handle levers including a proximal end and a distal end, the proximal end of the fifth opposed handle lever pivotally attached to the third opposed handle lever at a location proximate to the distal end of the third opposed handle lever and the proximal end of the sixth opposed handle lever pivotally attached to the fourth opposed handle lever at a location proximate to the distal end of the fourth opposed handle lever;

the fifth opposed handle lever including a first transverse opening extending through the fifth opposed handle lever, the first transverse opening located proximate to a pivot point of the third lever set; and the sixth opposed handle lever including a second transverse opening extending through the sixth opposed handle lever, the second transverse opening located proximate to said pivot point of the third lever set, and a releasable stop element, wherein the first and second levers are moveable between a first handle position, a second handle position and a third handle position along a range of handle motion, the second handle position being at least partially defined by the releasable stop element, the second handle position being between the first and third handle positions along the range of handle motion, and wherein the first and second transverse openings are substantially aligned for receiving a work piece to be cut therethrough when the first and second opposed handle levers are in the second handle position, and the first and second transverse openings rotate out of alignment for cutting the work piece received therethrough in a first relative direction when the first and second opposed handle levers are in the first handle position and the first and second transverse openings rotate out of alignment for cutting the work piece received therethrough in a second opposing relative direction when the first and second opposed handle levers are in the third handle position.

11. The surgical cutting tool of claim 10, wherein the second and third lever sets can be positioned in a first collapsed tool configuration with the second and third lever sets located between the first and second opposed handle levers of the first lever set when the first and second levers are in the first handle position along the range of handle motion, and the second and third lever sets can be positioned in a second expanded tool configuration with the second and third lever sets extending outward from the first and second opposed handle levers of the first lever set when the first and second levers are in a fourth handle position along the range of handle motion.

12. The surgical cutting tool of claim 10, wherein the releasable stop element comprises at least one member of the group consisting of a latch, a detent and a securing mechanism that mechanically engages when the first and second transverse openings are substantially aligned.

13. The surgical cutting tool of claim 10, wherein the fifth opposed lever set include at least one replaceable cutting insert.

14. The surgical cutting tool of claim 13, wherein the at least one replaceable cutting insert comprises a straight cutting insert.

15. The surgical cutting tool of claim 13, wherein the at least one replaceable cutting insert comprises a tapered cutting insert.

16. The surgical cutting tool of claim 10, wherein the first lever set includes a base.

17. The surgical cutting tool of claim 16, wherein the base is removeable from the first lever set.

18. A surgical cutting tool kit comprising:
a cutting tool including:
 a first lever set including first and second opposed handle levers in a second-order lever arrangement, each of said first and second opposed handle levers including a handle end having a modular handle attachment point and a pivot end;
 a second lever set pivotally attached to the first lever set, the second lever set including third and fourth opposed handle levers in a first-order arrangement, each of said third and fourth opposed handle levers including a proximal end and a distal end, the proximal end of the third opposed handle lever pivotally attached to the first opposed handle lever at a location between the handle and pivot ends of the first opposed handle lever and the proximal end of the fourth opposed handle lever pivotally attached to the second opposed handle lever at a location between the handle and pivot ends of the second opposed handle lever;
 a third lever set pivotally attached to the second lever set, the third lever set including fifth and sixth opposed handle levers in a first-order or second-order arrangement, each of said fifth and sixth opposed handle levers including a proximal end and a distal end, the proximal end of the fifth opposed handle lever pivotally attached to the third opposed handle lever at a location proximate to the distal end of the third opposed handle lever and the proximal end of the sixth opposed handle lever pivotally attached to the fourth opposed handle lever at a location proximate to the distal end of the fourth opposed handle lever;
 the fifth opposed handle lever including a first transverse opening extending through the fifth opposed handle lever, the first transverse opening located proximate to a pivot point of the third lever set; and
 the sixth opposed handle lever including a second transverse opening extending through the sixth opposed handle lever, the second transverse opening located proximate to said pivot point of the third lever set, and
 a releasable stop element,
 wherein the first and second levers are moveable between a first handle position, a second handle position and a third handle position along a range of handle motion, the second handle position being at least partially defined by the releasable stop element, the second handle position being between the first and third handle positions along the range of handle motion, and wherein the first and second transverse openings are substantially aligned for receiving a work piece to be cut therethrough when the first and second opposed handle levers are in the second handle position, and the first and second transverse openings rotate out of alignment for cutting the work piece received therethrough in a first relative direction when the first and second opposed handle levers are in the first handle position and the first and second transverse openings rotate out of alignment for cutting the work piece received therethrough in a second opposing relative direction when the first and second opposed handle levers are in the third handle position; and
a plurality of removeable handle portions of differing lengths; the plurality of removeable handle portions of differing lengths each including a connection mechanism for selectively mating with at least one modular handle point of the first and second opposed handle levers.

19. The surgical cutting tool kit of claim 18, wherein at least one of the plurality of removeable handle portions of differing lengths comprises a base.

20. The surgical cutting tool kit of claim 18, further comprising a plurality of replaceable cutting inserts, the cutting tool including at least one replaceable cutting insert on the fifth opposed lever set.

* * * * *